(12) United States Patent
Langley et al.

(10) Patent No.: US 11,219,448 B2
(45) Date of Patent: Jan. 11, 2022

(54) SYSTEMS AND METHODS FOR FIXING SOFT TISSUE

(71) Applicant: LMT, LLC, Portland, OR (US)

(72) Inventors: Graham C. Langley, Portland, OR (US); Jesse A. McCarron, Portland, OR (US)

(73) Assignee: LMT, LLC, Portland, OR (US)

( * ) Notice: Subject to any disclaimer, the term of this patent is extended or adjusted under 35 U.S.C. 154(b) by 0 days.

(21) Appl. No.: 16/268,254

(22) Filed: Feb. 5, 2019

(65) Prior Publication Data

US 2019/0167258 A1    Jun. 6, 2019

Related U.S. Application Data

(62) Division of application No. 15/164,616, filed on May 25, 2016, now Pat. No. 10,588,619.

(60) Provisional application No. 62/166,521, filed on May 26, 2015.

(51) Int. Cl.
| | |
|---|---|
| *A61B 17/04* | (2006.01) |
| *A61B 17/06* | (2006.01) |
| *A61B 17/11* | (2006.01) |
| *A61B 17/29* | (2006.01) |

(52) U.S. Cl.
CPC .... *A61B 17/0469* (2013.01); *A61B 17/06166* (2013.01); *A61B 17/1146* (2013.01); *A61B 17/29* (2013.01); *A61B 2017/0498* (2013.01); *A61B 2017/061* (2013.01); *A61B 2017/06042* (2013.01); *A61B 2017/06076* (2013.01);

(Continued)

(58) Field of Classification Search
CPC . A61B 17/0469; A61B 17/1146; A61B 17/29; A61B 2017/0498; A61B 2017/06042; A61B 17/06166; A61B 17/2841; A61B 17/0401; A61B 2017/06171; A61B 2017/086; A61F 2002/0847-0888
See application file for complete search history.

(56) References Cited

U.S. PATENT DOCUMENTS

| | | | |
|---|---|---|---|
| 5,562,685 A | | 8/1996 | Mollenauer et al. |
| 5,782,844 A | * | 7/1998 | Yoon .................... A61B 17/064 606/139 |

(Continued)

FOREIGN PATENT DOCUMENTS

| | | |
|---|---|---|
| DE | 1810800 A1 | 6/1970 |
| GB | 2482638 A | 2/2012 |
| JP | 2002-502658 | 1/2002 |

*Primary Examiner* — Erich G Herbermann
*Assistant Examiner* — Christina C Lauer
(74) *Attorney, Agent, or Firm* — Schwabe, Williamson & Wyatt, P.C.

(57) ABSTRACT

Embodiments of systems and methods for fixing soft tissue are disclosed herein. In some embodiments, soft tissue may be fixed to an attachment surface (such as bone, other soft tissue, other implants, or allograft or xenograft materials) by providing a helical suture in the soft tissue, wherein the soft tissue has a longitudinal axis along which the soft tissue undergoes tension under normal physiological conditions, and wherein a longitudinal axis of the helical suture in the soft tissue is oriented parallel to the longitudinal axis of the soft tissue; and securing the helical suture to an attachment surface.

22 Claims, 17 Drawing Sheets

(52) U.S. Cl.
CPC ............... *A61B 2017/06171* (2013.01); *A61B 2017/2932* (2013.01)

(56) References Cited

U.S. PATENT DOCUMENTS

| | | | | |
|---|---|---|---|---|
| 6,626,917 | B1* | 9/2003 | Craig | A61B 17/0401 606/144 |
| 6,984,241 | B2* | 1/2006 | Lubbers | A61B 17/0401 606/103 |
| 8,623,049 | B2* | 1/2014 | Ward | A61B 17/0401 606/232 |
| 2002/0111534 | A1* | 8/2002 | Suzuki | A61B 1/00098 600/102 |
| 2004/0002699 | A1 | 1/2004 | Ryan et al. | |
| 2004/0138704 | A1* | 7/2004 | Gambale | A61B 17/0469 606/213 |
| 2004/0147957 | A1* | 7/2004 | Pierson, III | A61B 17/0469 606/228 |
| 2005/0033367 | A1 | 2/2005 | Leung et al. | |
| 2007/0135843 | A1* | 6/2007 | Burkhart | A61B 17/0401 606/232 |
| 2012/0253365 | A1 | 10/2012 | Sikora et al. | |
| 2012/0296345 | A1* | 11/2012 | Wack | A61F 2/0811 606/139 |
| 2013/0296955 | A1 | 11/2013 | Haggerty et al. | |
| 2014/0088349 | A1 | 3/2014 | Alexander et al. | |

\* cited by examiner

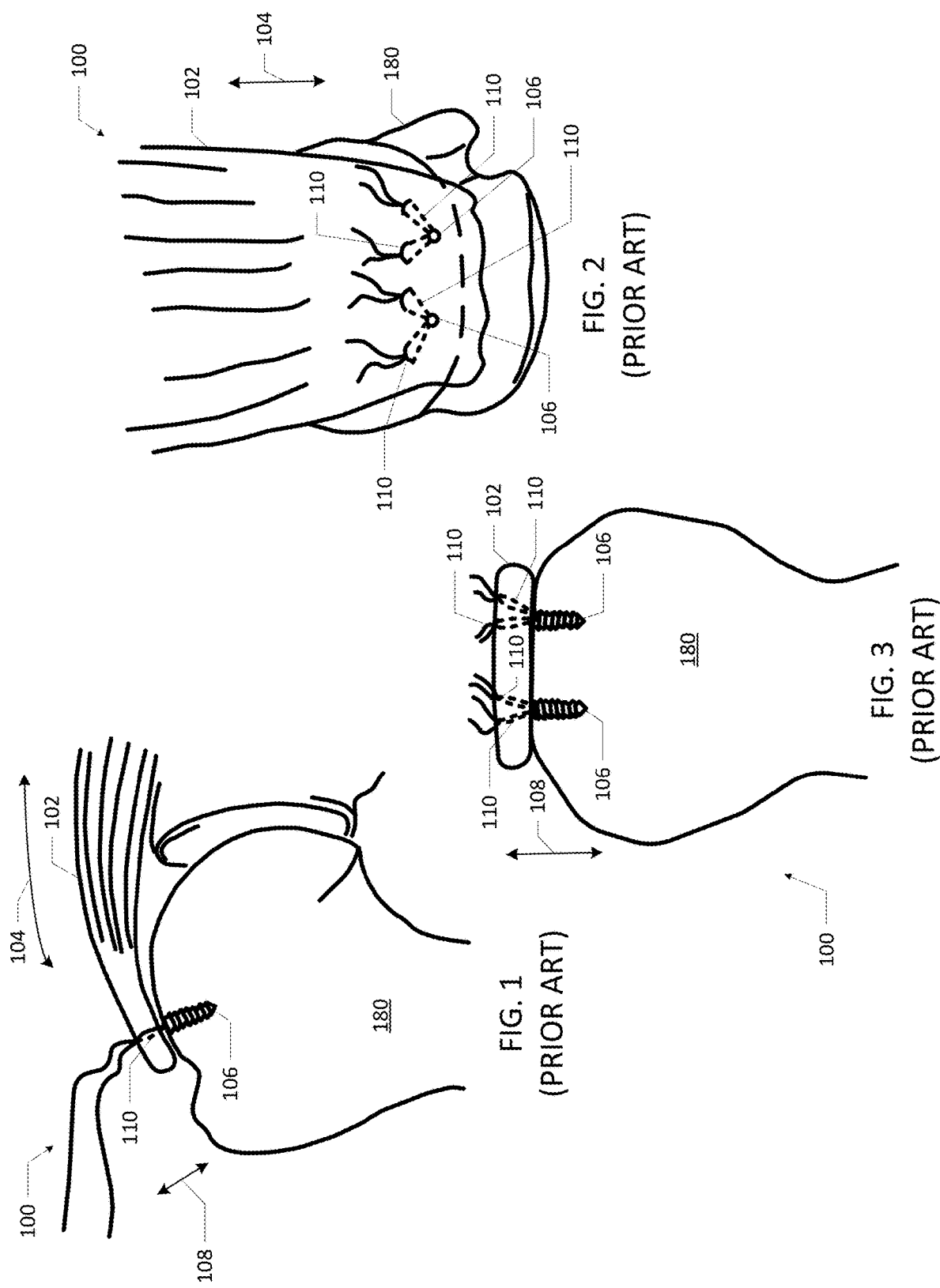

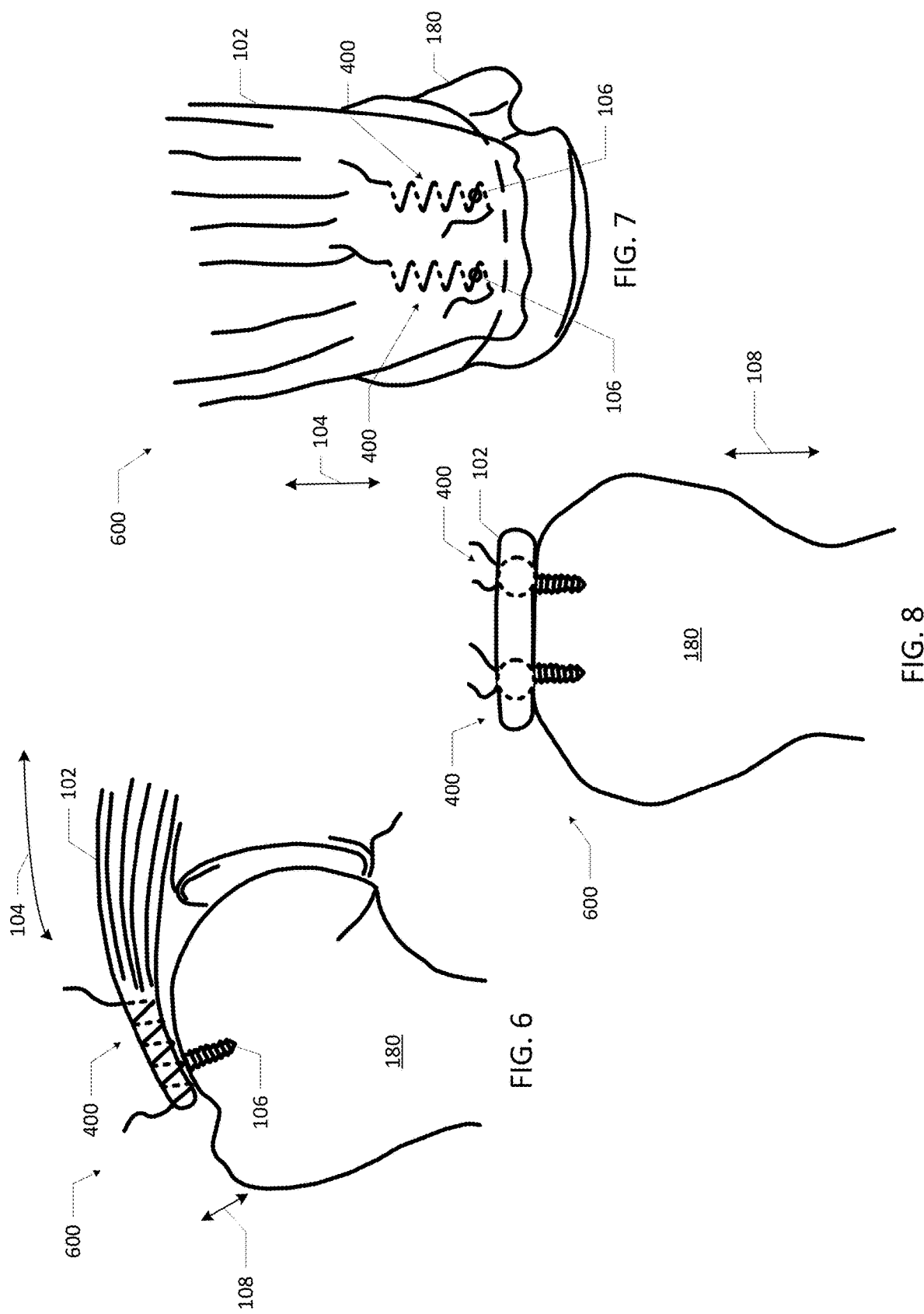

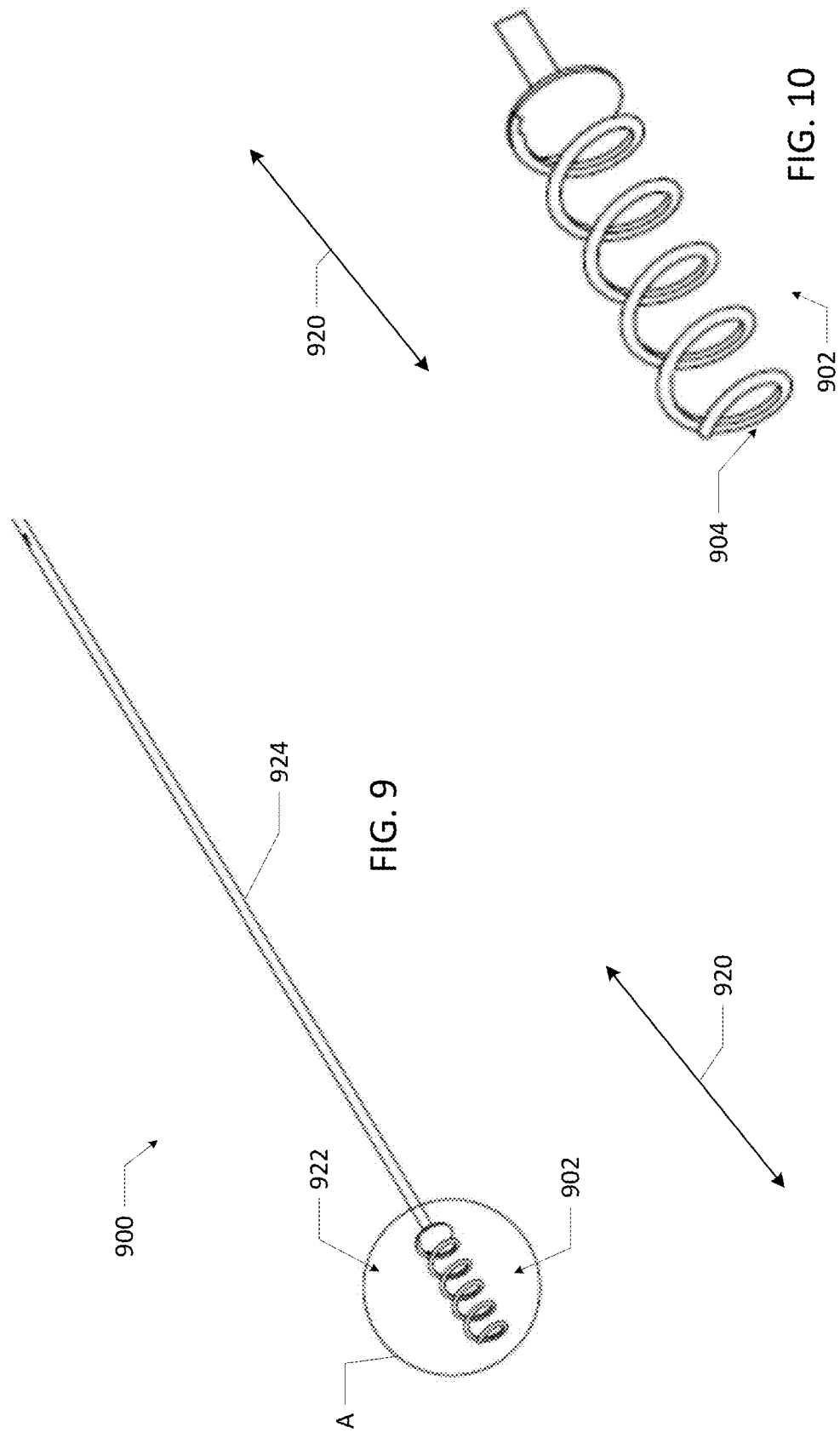

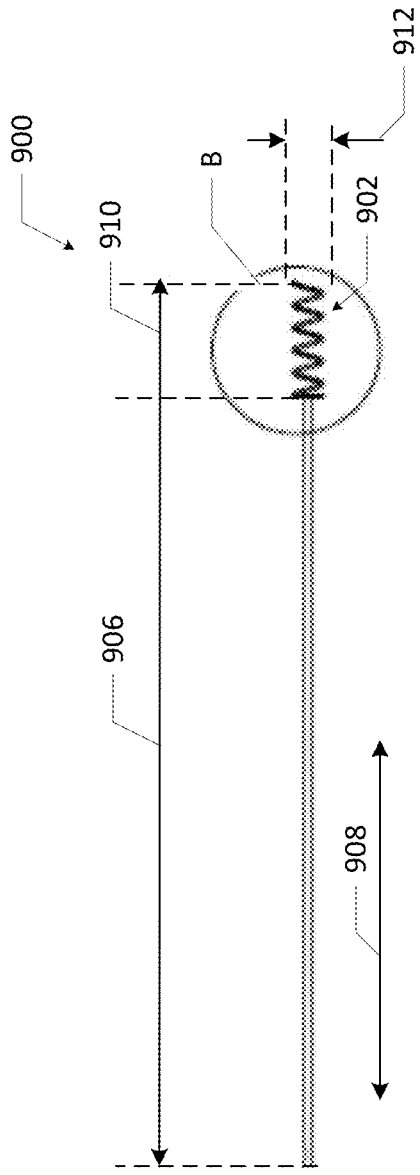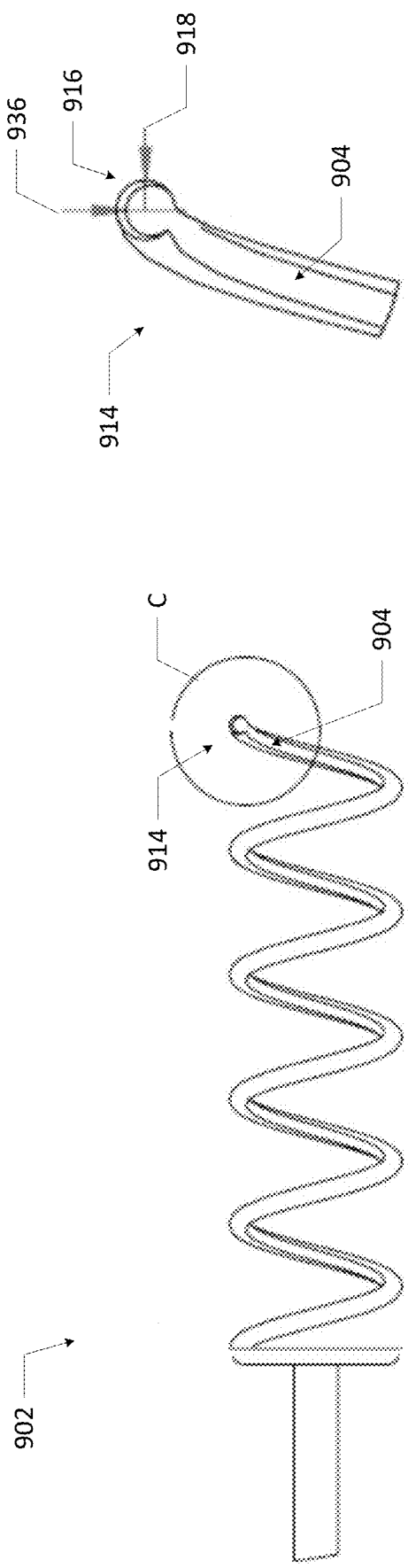
FIG. 11
FIG. 12
FIG. 13

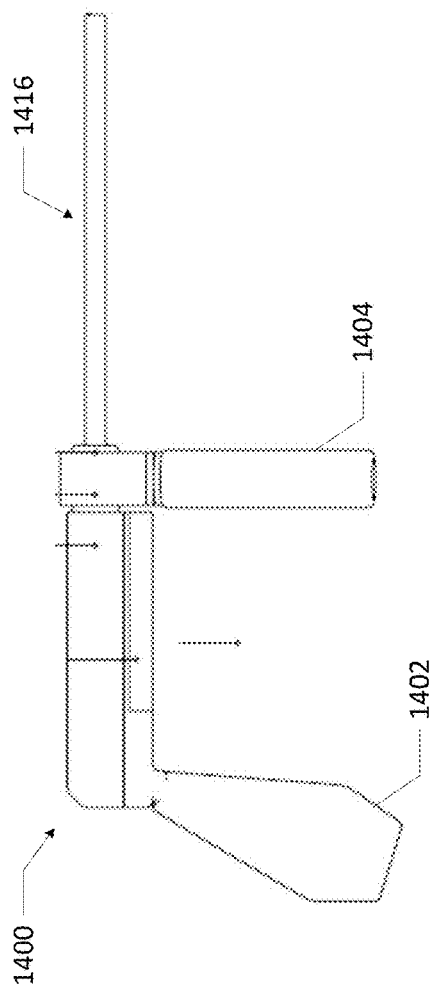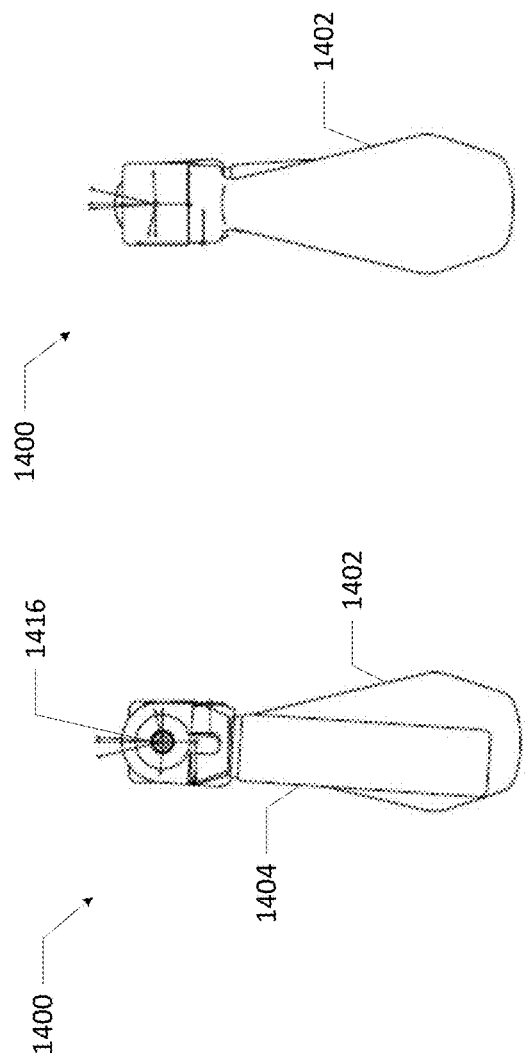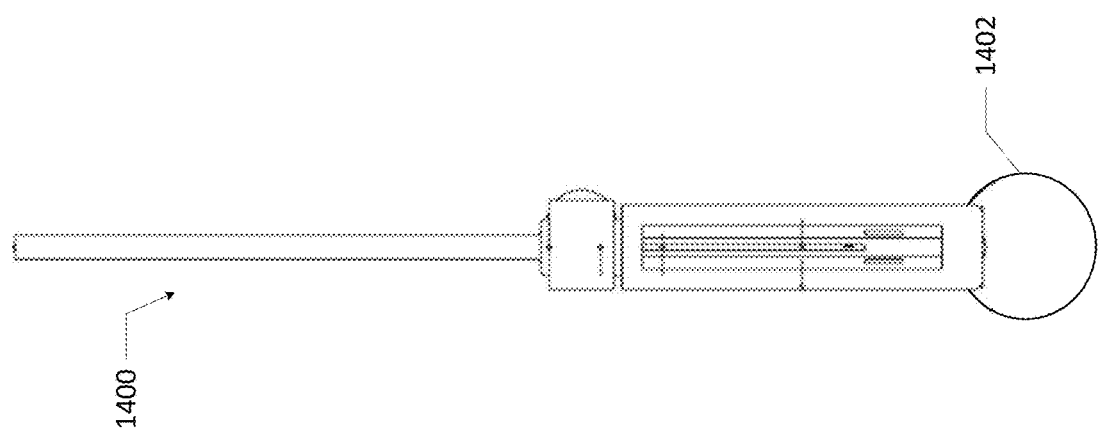

```
                    ┌─────────────────────────────────────┐
                    │ 2200                                │
                    └─────────────────────────────────────┘

┌──────────────────────────────────────────────────────────┐
│ Provide a helical suture in soft tissue, wherein the soft │
│ tissue has a longitudinal axis along which the soft      │
│ tissue undergoes tension under normal physiological       │
│ conditions, and wherein a longitudinal axis of the       │
│ helical suture in the soft tissue is oriented parallel to │
│ the longitudinal axis of the soft tissue                 │
│                         2202                              │
└──────────────────────────────────────────────────────────┘
                              │
                              ▼
┌──────────────────────────────────────────────────────────┐
│ Secure the helical suture to an attachment surface        │
│                         2204                              │
└──────────────────────────────────────────────────────────┘
```

FIG. 22

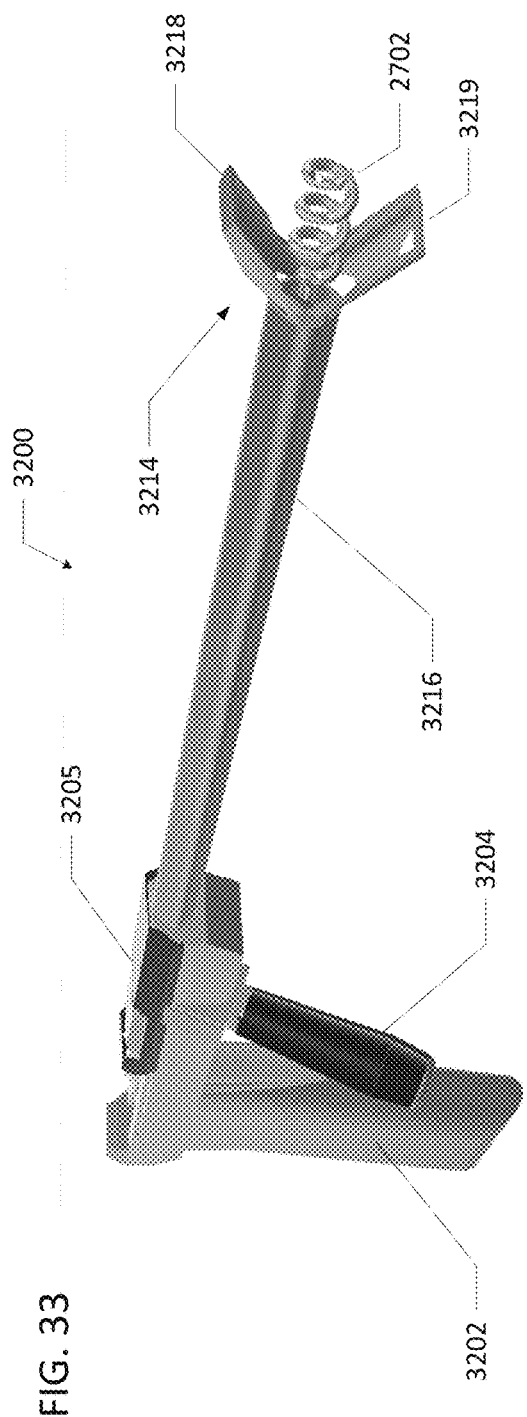

SYSTEMS AND METHODS FOR FIXING SOFT TISSUE

CROSS-REFERENCE TO RELATED APPLICATION

This application is a divisional of and claims the priority benefit of the earlier filing date of U.S. patent application Ser. No. 15/164,616, which claims priority to U.S. Provisional Patent Application No. 62/166,521, filed May 26, 2015, which are specifically incorporated herein by reference in their entirety.

TECHNICAL FIELD

The present disclosure relates generally to soft tissue repair, and more particularly, to systems and methods for fixing soft tissue to an attachment surface.

BACKGROUND

The conventional approach to soft tissue repair includes passing individual sutures through damaged tissue near the point of intended fixation. Current techniques require separate passage of the suture material each time the suture is passed through the soft tissue to be repaired (e.g., to secure that tissue to a bone or other attachment surface). These repairs are complex and time-consuming to perform, and fail frequently.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

FIGS. 1-3 are various views of a conventional suture arrangement for fixing soft tissue to bone in a typical rotator cuff repair performed in the shoulder for rotator cuff tear.

FIGS. 6-8 are various views of a suture arrangement including the helical suture of FIGS. 4-5 in a rotator cuff repair performed in the shoulder for rotator cuff tear, in accordance with various embodiments.

FIGS. 9-13 are various views of an insertion instrument for providing the helical suture of FIGS. 4-5 in soft tissue, in accordance with various embodiments.

FIGS. 14-19 are various views of another insertion instrument for providing the helical suture of FIGS. 4-5 in soft tissue, in accordance with various embodiments.

FIG. 22 is a flow diagram of an illustrative method for fixing soft tissue to an attachment surface, in accordance with various embodiments.

FIGS. 32-36 are various views of another insertion instrument for providing a helical suture in soft tissue, in accordance with various embodiments.

DETAILED DESCRIPTION

Figure 4:
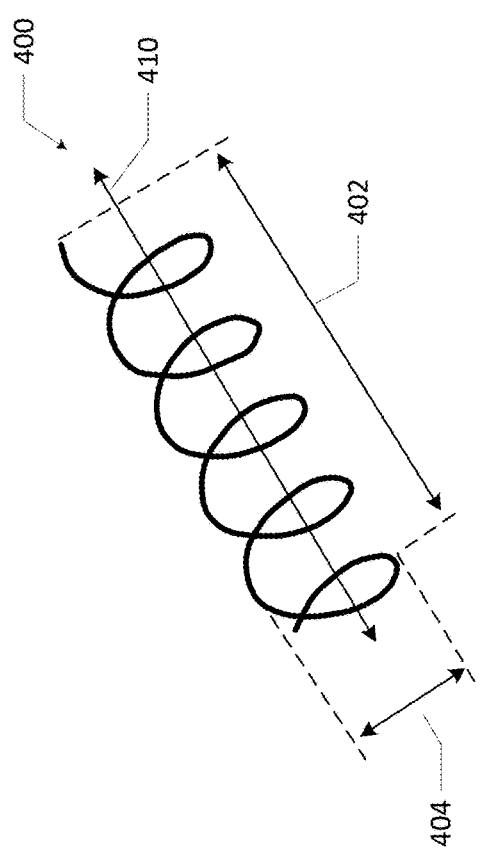
FIGS. 4-5 are various views of a helical suture, in accordance with various embodiments as it would sit within soft tissue under repair/reconstruction.

In the following detailed description, reference is made to the accompanying drawings that form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description uses the phrases "in an embodiment," or "in embodiments," which may each refer to one or more of the same or different embodiments. Furthermore, the terms "comprising," "including," "having," and the like, as used with respect to embodiments of the present disclosure, are synonymous.

Disclosed herein are methods, systems, and devices that introduce a new way to combat recurrent tissue retraction. Rather than implanting an anchor and passing a preloaded suture by way of individual knot tying and a multitude of instruments, the inventors have developed methods, systems, and devices that can use a single instrument to pass a suture in such a way that eliminates shearing of the tissue and instead distributes the holding forces in both the normal and tangential directions.

Embodiments of systems, devices, and methods for fixing soft tissue to an attachment surface are disclosed herein. For example, in some embodiments, soft tissue may be fixed to an attachment surface by providing one or more helical sutures, such as two helical sutures of opposite rotation or twist, in the soft tissue. In embodiments, the soft tissue has a longitudinal axis along which the soft tissue undergoes tension under normal physiological conditions, and the longitudinal axis of the helical suture in the soft tissue is oriented parallel to the longitudinal axis, or loading axis, of the soft tissue, such that the longitudinal axis of the helix of the suture is oriented parallel to the line of tension forces.

The systems, devices, and methods disclosed herein may provide significant advantages over conventional techniques. As noted above, conventional approaches to soft tissue repairs are complex and time-consuming to perform because each time the suture passes through the tissue, a separate maneuver is required. As a result, most suture repairs/reconstructions in soft tissue are limited to one (simple suture) or two (mattress suture) passes of the suture through the tissue to be repaired, near the edge of the tissue. These limited points of fixation for each suture result in high concentrations of stress in the repaired/reconstructed tissue edge where the suture is passing once or twice through the tissue. These high stress concentrations lead to a high rate of repair/reconstruction failure at the suture-tissue interface if the soft tissues are exposed to loading under tension.

The systems, devices, and methods disclosed herein provide useful medical devices and techniques that may be applied in any type of surgical procedure where soft tissue repair or reconstruction under tension is performed, (e.g. orthopedic surgical procedures where tendons are being repaired to bone, minimally invasive sports medicine, and soft tissue repair settings). More generally, the systems and methods disclosed herein may be usefully applied in any field or type of surgery in which soft tissues are to be repaired or reconstructed so that stresses in the repaired/reconstructed tissues are more widely and evenly distributed than conventionally achievable, resulting in decreased risk of repair/reconstruction failure at the suture-soft tissue interface (e.g., via suture cut-out).

The applications of the systems, devices, and methods disclosed herein could include, but are not limited to, repairs and reconstructions in soft tissue-to-bone, soft tissue-to-soft tissue, soft tissue-to-allograft/xenograft material, or soft tissue-to-synthetic material. Thus, the "attachment surfaces" referred to herein may include bone, soft tissue, allograft/xenograft material, synthetic material, any other suitable material, or a combination thereof. While bone may be used as an illustrative example of an attachment surface, the systems and methods disclosed herein may be applied to any suitable attachment surface.

Disclosed herein is a method for fixing soft tissue of a subject to an attachment surface, for example, bone. In embodiments, the method includes providing, and/or inserting, one or more helical suture(s), having a longitudinal axis, in the soft tissue of a subject. By longitudinal axis, it is meant herein the axis of the helical suture that runs down the center of the helix, that is axis which the helix rotate around and/or translates down as it progresses. The soft tissue may have a longitudinal axis, and/or loading axis and the one or more sutures are oriented with the longitudinal axis of the helical suture in the soft tissue parallel, or substantially parallel, to the longitudinal axis of the soft tissue, for example an axis that is undergoing tensional stress. To fix the soft tissue, the helical suture is attached to the attachment surface, for example by fixing the free end(s) of the helical suture(s) proximal the attachment surface to the attachment surface. The disclosed methods are particularly suited for fixing soft tissue that undergoes tension, under normal physiological conditions, along the tissue's longitudinal axis, for example a tendon. In some embodiments, the attachment surface includes bone, such as a humerus. In some embodiments, the attachment surface includes soft tissue, allograft material, xenograft material, or a synthetic material, or a combination thereof. In some embodiments, securing the helical suture to the attachment surface includes securing the helical suture to an anchor secured to, or in, the attachment surface, for example a bone screw or other device implanted or fastened to bone.

In some embodiments, the method includes providing at least two helical sutures, such as a first helical suture and a second helical suture. In such methods, the first and the second helical suture in the soft tissue are provided or inserted such that the longitudinal axis of the second helical suture is oriented substantially parallel to the longitudinal axis of the first helical suture. This second helical suture can be secured to the attachment surface, for example using the same or different anchor secured to the attachment surface. In some embodiments, the first helical suture and the second helical suture have opposite (or the same) direction of rotation, see, for example, FIGS. 37A-39. One advantage of using two helical sutures with opposite directions of rotation is that the torque of the sutures is effectively cancelled out. In certain embodiments, the first helical suture and the second helical suture overlap, for example when they have opposite directions of rotation, see, for example, FIG. 39.

In embodiments, providing or inserting a helical suture in soft tissue includes inserting a helix-shaped needle into the soft tissue, and rotating the helix-shaped needle to provide a helical channel in the soft tissue until the tip of the helix-shaped needle protrudes from the soft tissue. Suture material is secured to the tip of the helix-shaped needle, and the direction of rotation of the helix-shaped needle is reversed to retain the helical suture in the soft tissue. In certain embodiments, the helix-shaped needle is plunged into the soft tissue, such as a tendon, and, at full-deployment, the needle tip grasps the free suture by mechanical means of an eyelet. The helix-shaped needle then retrogrades the suture to the lateral opening of the tendon in the path of the helix-shaped needle by reversing the direction of rotation of the helix-shaped needle. In certain embodiments, a second helix-shaped needle with the opposite direction of rotation is used to provide a second helical suture mirroring the first. The two helices may overlap one another, creating a double helix. The two helices may be spaced apart, for example at different angles depending on the desired direction of grip. The process can be repeated as necessary. In embodiments, the two helical sutures are formed from the same piece of suture material. In some embodiment, the helical suture includes between 1 and 10 helical turns, such as at least two turns of suture material.

In certain embodiments, providing the helical suture in the soft tissue includes inserting a helix-shaped needle into the soft tissue, wherein suture material is secured to the helix-shaped needle, and rotating the helix-shaped needle to retain the helical suture in the soft tissue. In such embodiments, the suture material is pulled with the helix-shaped needle through the soft tissue.

In embodiments, rotating the helix-shaped needle may include grasping, with a hand of a human operator, an insertion instrument including the helix-shaped needle, and rotating the insertion instrument with the hand. In embodiments, rotating the helix-shaped needle includes linearly translating a slide component of an insertion instrument including the helix-shaped needle, wherein the linear translation of the slide component causes or results in rotation of the helix-shaped needle. In certain embodiments, linearly translating the slide component includes linearly translating a trigger lever away from, or toward, the soft tissue. In some embodiments, providing the helical suture in the soft tissue includes gripping, with a gripping portion of an insertion instrument including a helix-shaped needle, the soft tissue, and pulling, with the gripping portion, the soft tissue toward and over the helix-shaped needle while the helix-shaped needle rotates relative to the soft tissue and/or the gripping portion of the insertion instrument. In some embodiments of the method, the insertion instrument includes a trigger lever extending perpendicularly from a longitudinal axis of the helix-shaped needle, where rotating the trigger lever around the longitudinal axis of the helix-shaped needle causes the gripping portion to grip the soft tissue, and translating the trigger lever along the longitudinal axis of the helix-shaped needle and away from, or toward, the soft tissue causes the helix-shaped needle to rotate. In some embodiments the insertion instrument is electrically driven. In some embodiments, the helix-shaped needle is included in an insertion instrument having a rear handle, and the helix-shaped needle does not translate with reference to the rear handle when the helix-shaped needle is rotated to provide the helical suture in the soft tissue.

FIGS. 1-3 are various views of a conventional suture arrangement 100 for fixing soft tissue 102 to a bone 180 in a typical rotator cuff repair performed in the shoulder for rotator cuff tear. In particular, FIG. 1 is a side cross-sectional view of the suture arrangement 100, FIG. 2 is a top view of the suture arrangement 100, and FIG. 3 is a front cross-sectional view of the suture arrangement 100.

In the suture arrangement 100, one or more anchors 106 may be screwed into or otherwise secured in the bone 180, and one or more sutures 110 may be attached to both the soft tissue 102 and the anchor 106 to attach the soft tissue 102 to the bone 180. The anchor 106 may be, for example, a metal or bio-absorbable anchor. The sutures 110 are typically oriented substantially parallel to the axis 108 illustrated in FIGS. 1 and 3. The axis 108 is perpendicular to a longitudinal axis 104 of the soft tissue 102 (along which is exerted the bulk of the tensive forces experienced by the soft tissue 102 under normal physiological conditions in which the soft tissue 102 is attached to the bone 180). Typically, the anchors 106 are preloaded with one or multiple sutures 110. The anchors 106 are an example of a device for "linking" the suture 110 in the soft tissue 102 to the bone 180, but any other device for achieving such a purpose may be used.

Figure 5:
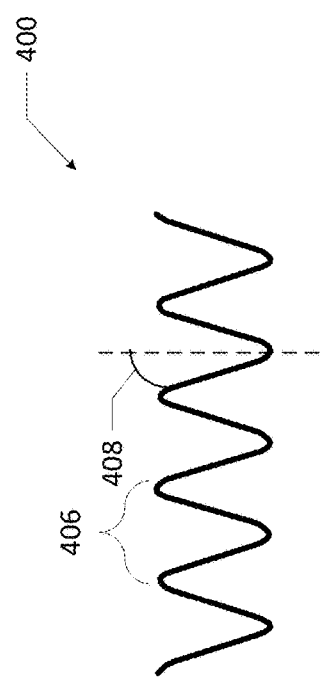

FIGS. 4 and 5 are various views of a helical suture 400 as it would sit in soft tissue after application, in accordance with various embodiments disclosed herein. In particular, FIG. 4 is a perspective view of the helical suture 400 and FIG. 5 is a side view of the helical suture 400. The helical suture 400 may have a length 402 along the longitudinal axis 410 of the helical suture 400. The length 402 may take any suitable value. In some embodiments, the length 402 of the helical suture 400 may be between approximately 10 and approximately 30 millimeters (e.g., +/− 2 millimeters). For example, the length 402 of the helical suture may be approximately 20 millimeters (e.g., +/− 2 millimeters). The helical suture 400 may have a diameter 404, which may take any suitable value, for example for suture material. In some embodiments, the diameter 404 of the helical suture 400 may be between approximately 3 and approximately 8 millimeters (e.g., +/− 1 millimeter). For example, the diameter 404 may be approximately 5.5 millimeters (e.g., +/− 1 millimeter).

The helical suture 400 may be formed of any suitable suture material, of which many conventional examples exist. For example, the suture material may be a #2 (0.6 millimeter diameter) braided filament having a solid inner polymer core with a "braided" outer layer. The outer layer is generally a much thinner polymer. An appropriate suture material may be smaller or wider than 0.6 millimeters in diameter, and the appropriate size and material may depend on the type of repair.

The helical suture 400 may have any desired number of turns 406 or fractions thereof (wherein a turn is defined herein as a portion of the coil traversing 360 degrees, as illustrated by the turn 406 in FIG. 5). In some embodiments, the helical suture 400 may have 1-6 turns or fractional increments thereof, such as about 1, about 2, about 3, about 4, about 5, about 6 or, in some cases more than 6 turns. For example, the helical suture 400 may include at least one, at least two, at least three, at least four, or at least five turns of suture material.

The helical suture 400 may have any desired turn angle 408 (wherein a turn angle is defined herein with respect to a reference line perpendicular to the longitudinal axis 410, as illustrated by the turn angle 408 in FIG. 5). In some embodiments, the turn angle 408 may be between approximately 20 and approximately 70 degrees (e.g., +/− 5 degrees). For example, the turn angle 408 may be approximately 45 degrees (e.g., +/− 5 degrees). The turn angle 408 need not be constant along the helical suture 400; instead, in some embodiments, the turn angle 408 may vary along the helical suture 400. Additionally, as discussed below, the turn angle 408 of the helical suture 400 may change as the underlying soft tissue 102 undergoes various forces (e.g., tension, contraction, or movement of the soft tissue). Thus, the turn angle 408 may refer to the turn angle imparted to the helical suture 400 when the helical suture 400 is first provided in the soft tissue 102, even though the turn angle 408 may change as the underlying soft tissue 102 deforms after provision. The length of suture material required to form a helical suture 400 will depend on the desired geometry of the helical suture 400, such as the length 402, the diameter 404, the number of turns 406, and/or the turn angle 408.

Exemplary helical sutures were tested against a massive cuff stitch (which is considered to be one of the strongest traditional stitch configurations in rotator cuff tendon tissue). These tests were performed in bovine tendon tissue comparing ultimate failure loads between these 2 suture configurations mounted in a uniaxial testing machine with a 1000 Newton (N) load cell. Testing protocol conformed with numerous previously published methodologies: Ten Newtons pre-load followed by a stepwise cyclic loading protocol to 180 (N) followed by 350 (N) at a rate of 0.25 Hz until complete structure failure occurred (defined as ultimate load). In this biomechanical testing it was found that, in terms of gross strength increase (ultimate load), the coil was ≉370% stronger (3.7×) than the massive cuff stitch. Average maximum load of coil was 336.8 N compared to 63.7 N for massive cuff stitch.

The relevant parameters for the helical suture are provided, including the total length in suture implanted, the total area enclosed by both, and the ultimate failure load.

Dimensionalities/Variables

T=3; number of turns in construct
D=5; Diameter in millimeters
H=12; Total height (depth in this case) of construct
r=2.5; Radius of construct Equation for Arc Length $$\text{Length} = 2 \ast (T \ast \text{sqrt}((pi \ast D)^2 + (H/T)^2)) \qquad (2)$$

Area enclosed by r-coil $$\text{Area} = 2 \ast ((2 \ast pi \ast r \ast H) + (2 \ast pi \ast r^2)) \qquad (1)$$

Length=97.2556 mm
Area=455.5309 mm^2

FIGS. 6-8 are various views of a suture arrangement 600 including the helical suture 400 of FIGS. 4-5 in a rotator cuff repair performed in the shoulder for rotator cuff tear, in accordance with various embodiments. In particular, FIG. 6 is a side cross-sectional view of the suture arrangement 600, FIG. 7 is a top view of the suture arrangement 600, and FIG. 8 is a front cross-sectional view of the suture arrangement 600.

In the suture arrangement 600, one or more anchors 106 may be screwed into or otherwise secured in the bone 180 (as discussed above with reference to the suture arrangement 100 of FIGS. 1-3). This scenario outlines the method for rotator cuff repair (an example clinical application), in which one or more anchors 106 may be implanted into the medial edge of the tendon footprint on the lateral aspect of the humeral head. One or more helical sutures 400 may be attached to both the soft tissue 102 and the anchor 106 to attach the soft tissue 102 to the bone 180. In particular, a helical suture 400 may be oriented in the soft tissue 102 such that the longitudinal axis 410 (FIG. 4) of the helical suture 400 is oriented parallel to the longitudinal axis 104 of the soft tissue 102. Thus, unlike the conventional suture 110 of FIGS. 1-3, in which the soft tissue 102 is fixed by the suture 110 at only one or two small, finite points, the bulk of the suture material of the helical suture 400 is distributed along the longitudinal axis 104 of the soft tissue 102 (in the direction in which tension is typically experienced by the soft tissue 102 under normal physiological conditions).

As shown in FIGS. 7 and 8, the suture arrangement 600 may include more than one helical suture 400 (e.g., the two sutures 400 illustrated in FIGS. 7 and 8). In other embodiments, a single helical suture 400 may be used, or two or more helical sutures 400, such as three or more, may be used. All of the helical sutures 400 included in a multiple helical suture arrangement may be oriented substantially in parallel (e.g., having their longitudinal axes 410 substantially parallel to the longitudinal axis 104 of the soft tissue 102) or may be oriented at any desired orientation with respect to each other. As discussed latter, with respect to FIGS. 37A-39, a single strand of suture material can be used to form two or more helical sutures. For example having the same or opposite helical rotations.

In some embodiments, the soft tissue 102 may be a tendon. In some embodiments, the bone 108 may be a humerus. Other examples of soft tissue repair to bone in which the systems and methods disclosed herein could be applied may include, but are not limited to, quadraceps and patella tendon repairs to the patella (knee cap), Achilles tendon repair, bicep tenodesis repair, pectoralis major tendon repairs to the humerus; and ligament repairs including, but not limited to, repair of the lateral ulnar collateral ligament at the elbow/distal humerus. Any mid-substance soft tissue rupture such as mid-substance ligament tears, or mid-substance tendon tears are also amenable to systems and methods in which helical suture configurations (e.g., arrangements including one or more helical suture 400) are placed into both sides of the tear, and repair of the defect is achieved by tightening and tying together the free ends of the sutures from each side of the tear. Non-tendon or ligament examples of surgical application include abdominal hernia repairs.

As illustrated in FIGS. 6-8, the helical suture 400 provides multiple loops of suture material through the soft tissue 102, with the primary distribution pattern of the suture material through the soft tissue 102 oriented in a helix running parallel to the primary direction of tension/loading in the soft tissue 102. The helical suture 400, when used in this manner, may distribute stress more broadly and evenly through the soft tissue 102 than the conventional sutures 110 discussed above with reference to FIGS. 1-3. This may reduce the likelihood of repair failures that can occur using conventional approaches, for example due to tension overload at the suture-tissue interface (leading to the suture cutting through the repaired tissue).

In particular, conventional sutures (e.g., using a simple stitch, a mattress stitch, a modified Mason-Allen stitch, or a massive cuff stitch) employ single-point fixation for each suture. Such sutures pass through soft tissue as few as one time, or a maximum of four times, all performed in a small area where the tendon is "spot welded" to the attachment surface. As these repairs are exposed to stress (in particular, tension) after surgery, the suture often cuts through the tendon in a similar manner as cheese wire cuts through a block of cheese. The result is the loss of tendon fixation and failure of the repair because stresses within the tissue are focused over too small an area of tissue, confined to the lateral edge of the tendon directly over the site of tendon-to-bone fixation. It is suggested that even when complete repair failure does not occur after rotator cuff repair surgery, the majority of conventional repairs at least partially fail (in that the suture slips at least partially through the tendon). Both partial and complete repair failures result in persistent pain and disability for patients and/or the need for further surgical intervention. Additionally, passing conventional sutures through soft tissue and tying them to hold the tissue to its attachment point are complex and time-consuming procedures that are not always executed successfully.

Use of the helical sutures 400 disclosed herein may reduce the incidence of repair failures after soft tissue repair surgeries (e.g., rotator cuff repair) by reducing the incidence of suture cut-through of the soft tissue. Various embodiments of the helical sutures disclosed herein may provide a broader (e.g., spread out) and more even distribution of stress within the repaired tissue in one or more ways. For example, the helical suture 400 may present a greatly increased number of points of suture-soft tissue interface relative to conventional sutures, distributing forces more broadly in the soft tissue. By positioning the helical suture 400 so that it extends medially into the soft tissue, forces experienced by the helical suture 400 may be distributed and dissipated by the medial tissue, rather than being entirely concentrated in the most lateral portion of the tissue being repaired (the conventional result). Additionally, when the soft tissue undergoes deformation due to tension forces and the helical suture 400 "lengthens" as a result, the helical suture 400 directs the tension forces both normally (into the tissue "inside" the helical suture 400 to compress that tissue) and tangentially (in the directions tangent to the helical suture 400). This distribution of forces may improve the "grip" of the helical suture 400 on the soft tissue when the soft tissue undergoes tension, reducing the likelihood of repair failure.

Additionally, use of various ones of the helical sutures 400 disclosed herein may eliminate or reduce the need for tying or significant suture management during surgery, as well as provide a significantly stronger repair construct than conventionally achievable.

The helical suture 400 may be provided to the soft tissue 102 using any suitable technique. For example, the helical suture 400 may be provided to the soft tissue 102 using a full open or minimally invasive (e.g., arthroscopic or laparoscopic) surgical technique. For example, a rotator cuff repair may be performed through a 4-10 centimeter skin incision or arthroscopically through 4-8 small 0.5 centimeter skin incisions. A rotator cuff repair may include two suture anchors and accompanying helical sutures 400, although more may be implanted when the quality of the soft tissue 102 is poor, or the tear is larger.

In some embodiments, the helical suture 400 may be provided to the soft tissue 102 using an insertion instrument designed for the rapid and accurate provision of the helical suture 400. For example, FIGS. 9-13 are various views of an insertion instrument 900 for providing the helical suture 400 in the soft tissue 102, in accordance with various embodiments (FIGS. 27-39, discussed below are various views of an alternative insertion instrument for providing the helical suture in the soft tissue, in accordance with various embodiments). In particular, FIG. 9 is a perspective view of the insertion instrument 900, FIG. 10 is a detailed view of the helix-shaped needle 902 (as indicated by circle A of FIG. 9), FIG. 11 is a side view of the insertion instrument 900, FIG. 12 is a detailed side view of the helix-shaped needle 902 (as indicated by circle B of FIG. 11), and FIG. 13 is a detailed side view of the end 914 of the helix-shaped needle 902 (as indicated by circle C of FIG. 12).

The insertion instrument 900 may have an extended body 924 that substantially defines the longitudinal axis 908 of the insertion instrument 900. The insertion instrument 900 may be formed of one or more materials, such as plastics and/or metals (e.g., medical grade titanium or aluminum). The insertion instrument 900 may also include a helix-shaped needle 902 at one end 922 of the body 924. The helix-shaped needle 902 may have a longitudinal axis 920 that is parallel with (e.g., coextensive with) the longitudinal axis 908 of the insertion instrument 900. The helix-shaped needle 902 may have a cutting tip for cutting into soft tissue, or the helix-shaped needle 902 may be loaded with a suture material having a toggle with a cutting tip, as discussed below with reference to FIGS. 20-21.

The body 924 of the insertion instrument 900 may have a length 906, which may be any suitable value. In some embodiments, the length 906 may be between approximately 100 and approximately 180 millimeters (e.g., +/− 10 millimeters). For example, the length 906 may be approximately 140 millimeters (e.g., +/− 10 millimeters).

Since the dimensions of the helix-shaped needle 902 substantially determine the dimensions of the helical suture 400 provided by use of the insertion instrument 900 (as discussed below), the dimensions of the helix-shaped needle 902 may be selected to achieve desired dimensions of the helical suture 400. For example, the helix-shaped needle 902 may have a length 910, which may be any suitable value. In some embodiments, the length 910 may be between approximately 10 and approximately 30 millimeters (e.g., +/− 2 millimeters). For example, the length 910 may be approximately 20 millimeters (e.g., +/− 2 millimeters). The helix-shaped needle 902 may have a diameter 912, which may be any suitable value. For example, in some embodiments, the diameter 912 may be between approximately 3 and approximately 8 millimeters (e.g., +/− 1 millimeter). In some embodiments, the diameter 912 may be approximately 5.5 millimeters (e.g., +/− 1 millimeter).

Suture material may be secured to the helix-shaped needle 902 such that, as the helix-shaped needle 902 is moved through the soft tissue 102, the suture material follows the path of the helix-shaped needle 902 to form the helical suture 400. As shown in FIGS. 10, 12, and 13, the helix-shaped needle 902 may have a recess 904 in which suture material (not shown) may be disposed. The dimensions of the recess 904 may be selected based on the properties of the soft tissue through which the helix-shaped needle 902 is to pass and/or the dimensions of the suture material to be disposed inside the recess 904. In some embodiments, an inner radius 936 of the recess 904 may be between approximately 0.1 and approximately 0.4 millimeters (e.g., +/− 0.03 millimeters). For example, the inner radius 936 may be approximately 0.26 millimeters (e.g., +/− 0.03 millimeters). An outer radius 918 of the helix-shaped needle 902 may be selected based on the properties of the soft tissue through which the helix-shaped needle 902 is to pass, the dimensions of the suture material to be disposed inside the recess 904, and/or the property of the material forming the helix-shaped needle 902 (e.g., with thicker "walls" appropriate for weaker materials). In some embodiments, the outer radius 918 of the helix-shaped needle 902 may be between approximately 0.2 and approximately 0.4 millimeters (e.g., +/− 0.03 millimeters). For example, the outer radius 918 of the helix-shaped needle 902 may be approximately 0.3 millimeters (e.g., +/− 0.03 millimeters). In another example, a helix-shaped needle 902 with an inner radius of approximately 0.3 millimeters and an outer radius of approximately 0.35 millimeters may be appropriate to contain a #2 suture material.

An end 914 of the helix-shaped needle 902 may have an opening 916 into which suture material may be inserted and retained within the recess 904 during use of the insertion instrument 900 to form the helical suture 400 with the suture material. As discussed below with reference to FIGS. 20 and 21, the suture material may have a tip that may serve as a tip of the helix-shaped needle 902 when the suture material is disposed in the recess 904 of the insertion instrument 900. The tip of the suture material may also serve as a toggle to hold the helical suture 400 in place in the soft tissue 102 after the helical suture 400 has been formed and the insertion instrument 900 has been removed.

The insertion instrument 900 may be used to provide a helical suture 400 to the soft tissue 102 by having a human operator grasp the body 924 with her hand, insert the helix-shaped needle 902 into the soft tissue 102 (with suture material secured to the helix-shaped needle 902), and rotate the helix-shaped needle 902 to move the helix-shaped needle 902 and the suture material through the soft tissue 102 to form the helical suture 400. When insertion is complete, an end of the suture material proximate to the end 914 of the helix-shaped needle 902 may be secured within or external to the soft tissue 102 (e.g., by grasping the end with an arthroscopic suture grasper, or as discussed below with reference to FIGS. 20 and 21) and the insertion instrument 900 may be removed by rotating the insertion instrument 900 in the reverse direction, leaving the helical suture 400 behind. Removal of the insertion instrument 900 from the soft tissue 102 may also pull the helical suture 400 "taut," providing a uniform and correct amount of tension in each turn of the helical suture 400. In some examples, the suture is pulled taught by the human operator, for example by applying a load to the suture material that extends from the soft tissue, for example a load of about 5 N to about 20 N, such that the helical suture is tightened in the tissue. A tensiometer can be used to measure the tension, such that this is not over-applied, for example a tensiometer that provides a visual or audible indication of proper tension. Such a tensiometer could be coupled to any of the devices disclosed herein.

Figure 27:
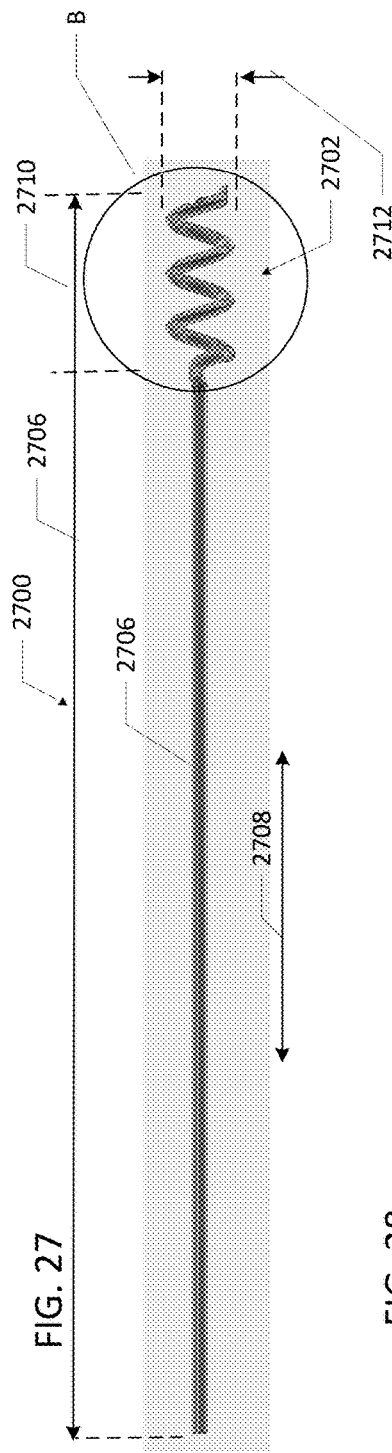
FIGS. 27-31 are various views of an insertion instrument for providing a helical suture in soft tissue, in accordance with various embodiments.
Figure 28:
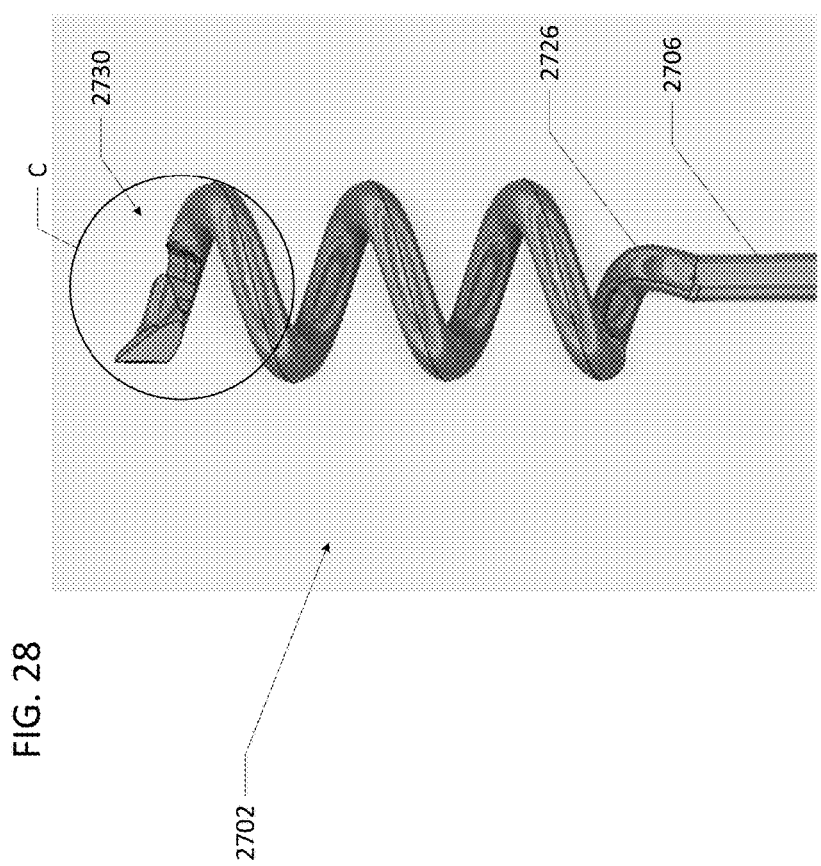
Figure 29:
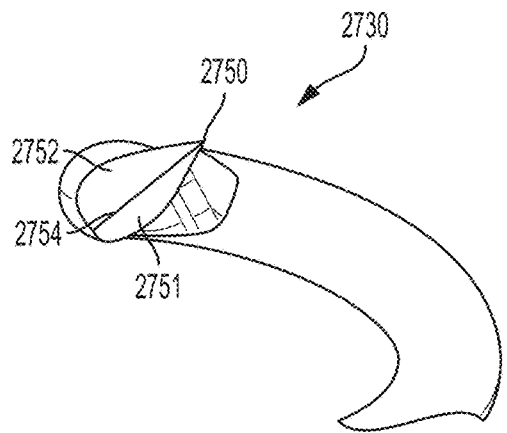
Figure 30:
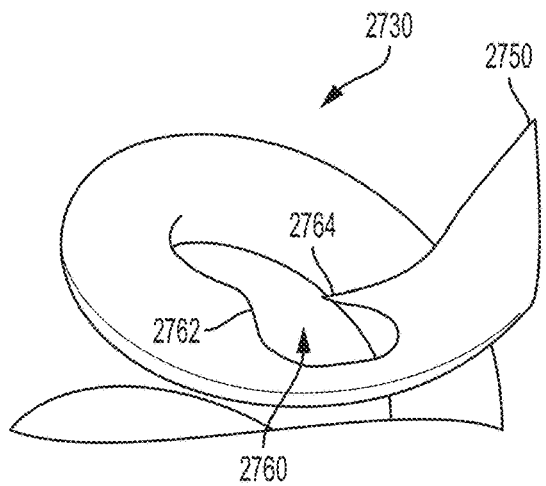
Figure 31:
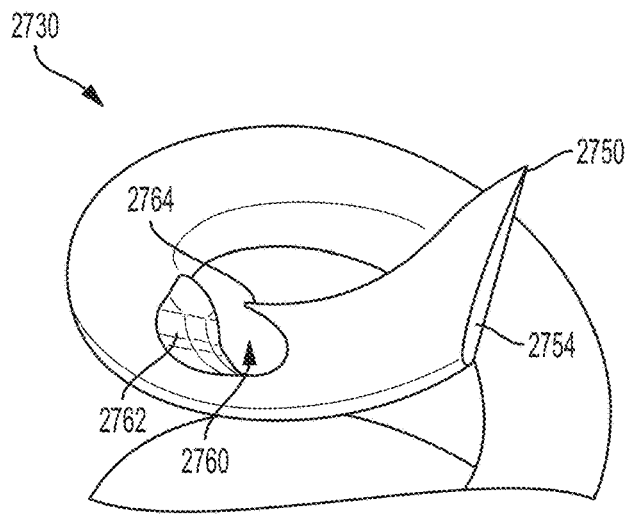

FIGS. 27-31, are various views of an alternative insertion instrument 2700 for providing the helical suture 400 in the soft tissue 102, in accordance with various embodiments. FIG. 27 is a side view of the insertion instrument 2700, FIG. 28 is a detailed side view of the helix-shaped needle 2702 (as indicated by circle B of FIG. 27), and FIGS. 29-31 are detailed perspective views of the end 2714 of the helix-shaped needle 2702 (as indicated by circle C of FIG. 28). As discussed below, a difference between the insertion instrument 900 and the insertion instrument 2700 is how the suture is passed through the tissue.

The insertion instrument 2700 may have an extended body 2724 that substantially defines the longitudinal axis 2708 of the insertion instrument 2700. The insertion instrument 2700 may be formed of one or more materials, such as plastics and/or metals (e.g., medical grade titanium or aluminum). The insertion instrument 2700 may also include a helix-shaped needle 2702 at one end of the body 2706 connected by bend 2726. The helix-shaped needle 2702 may have a longitudinal axis that is parallel with (e.g., coextensive with) the longitudinal axis 2708 of the insertion instrument 2700. The helix-shaped needle 2702 may have a cutting tip 2750 for cutting into soft tissue.

The body 2724 of the insertion instrument 2700 may have a length 2706, which may be any suitable value. In some embodiments, the length 2706 may be between approximately 100 and approximately 180 millimeters (e.g., +/− 10 millimeters). For example, the length 2706 may be approximately 140 millimeters (e.g., +/− 10 millimeters).

Since the dimensions of the helix-shaped needle 2702 substantially determine the dimensions of the helical suture 400 provided by use of the insertion instrument 2700 (as discussed below), the dimensions of the helix-shaped needle 2702 may be selected to achieve desired dimensions of the helical suture 400. For example, the helix-shaped needle 2702 may have a length 2710, which may be any suitable value. In some embodiments, the length 2710 may be between approximately 10 and approximately 30 millimeters (e.g., +/− 2 millimeters). For example, the length 2710 may be approximately 20 millimeters (e.g., +/− 2 millimeters). The helix-shaped needle 2702 may have a diameter 2712, which may be any suitable value. For example, in some embodiments, the diameter 2712 may be between approximately 3 and approximately 8 millimeters (e.g., +/− 1 millimeter). In some embodiments, the diameter 2712 may be approximately 5.5 millimeters (e.g., +/− 1 millimeter).

As the helix-shaped needle 2702 is moved through the soft tissue 102, a channel is formed in the soft tissue 102. Once the cutting tip 2750 pierces the outer surface of the soft tissue 102, suitable suture material is coupled to the cutting tip 2750 in recess 2760 by looping, or otherwise securing the suture material over hook 2764. As the helical-shaped needle 2702 is backed out of the soft tissue 102, the suture material follows the path of the helix-shaped needle 2702 in the channel to form the helical suture 400. As shown in FIGS. 29-31, the helix-shaped needle 2702 may have a recess 2760 in which suture material (not shown) may be disposed. The dimensions of the recess 2760 may be selected based on the properties and/or the dimensions of the suture material to be disposed inside the recess 2760. In some embodiments, the depth of the recess 2760 may be between approximately 0.1 and approximately 0.4 millimeters (e.g., +/− 0.03 millimeters). An outer radius of the helix-shaped needle 2702 may be selected based on the properties of the soft tissue through which the helix-shaped needle 2702 is to pass, the dimensions of the suture material to be disposed inside the recess 2760, and/or the property of the material forming the helix-shaped needle 2702. In some embodiments, the outer radius of the helix-shaped needle 2702 may be between approximately 0.2 and approximately 0.4 millimeters (e.g., +/− 0.03 millimeters). For example, the outer radius of the helix-shaped needle 2702 may be approximately 0.3 millimeters (e.g., +/− 0.03 millimeters).

The recess 2760 preferably has a hook like structure 2764 to grasp or hold the suture material.

The cutting tip 2750 of the helix-shaped needle 2702 may have any suitable cutting shape, although a shape with two planes 2751 and 2752 is shown bisected by a cutting ridge 2754.

The insertion instrument 2700 may be used to provide a helical suture 400 to the soft tissue 102 by having a human operator grasp the body 2724 with her hand, insert the helix-shaped needle 2702 into the soft tissue 102 (with suture material secured to the helix-shaped needle 902), and rotate the helix-shaped needle 2702 to move the helix-shaped needle 2702 through the soft tissue 102 to form the helical suture 400. When insertion is complete, the cutting tip 2750 protruding through the soft tissue 102 secures suitable suture material with hook 2764 of recess 2760, and the insertion instrument 2700 may be removed by rotating the insertion instrument 2700 in the reverse direction, leaving the helical suture 400 behind. Removal of the insertion instrument 900 from the soft tissue 102 may also pull the helical suture 400 "taut," providing a uniform and correct amount of tension in each turn of the helical suture 400. In some examples, the suture is pulled taught by the human operator, for example by applying a load to the suture material that extends from the soft tissue, for example a load of about 5 N to about 20 N, such that the helical suture is tightened in the tissue. A tensiometer can be used to measure the tension, such that this is not over-applied, for example a tensiometer that provides a visual or audible indication of proper tension. Such a tensiometer could be coupled to any of the devices disclosed herein.

Figure 14:
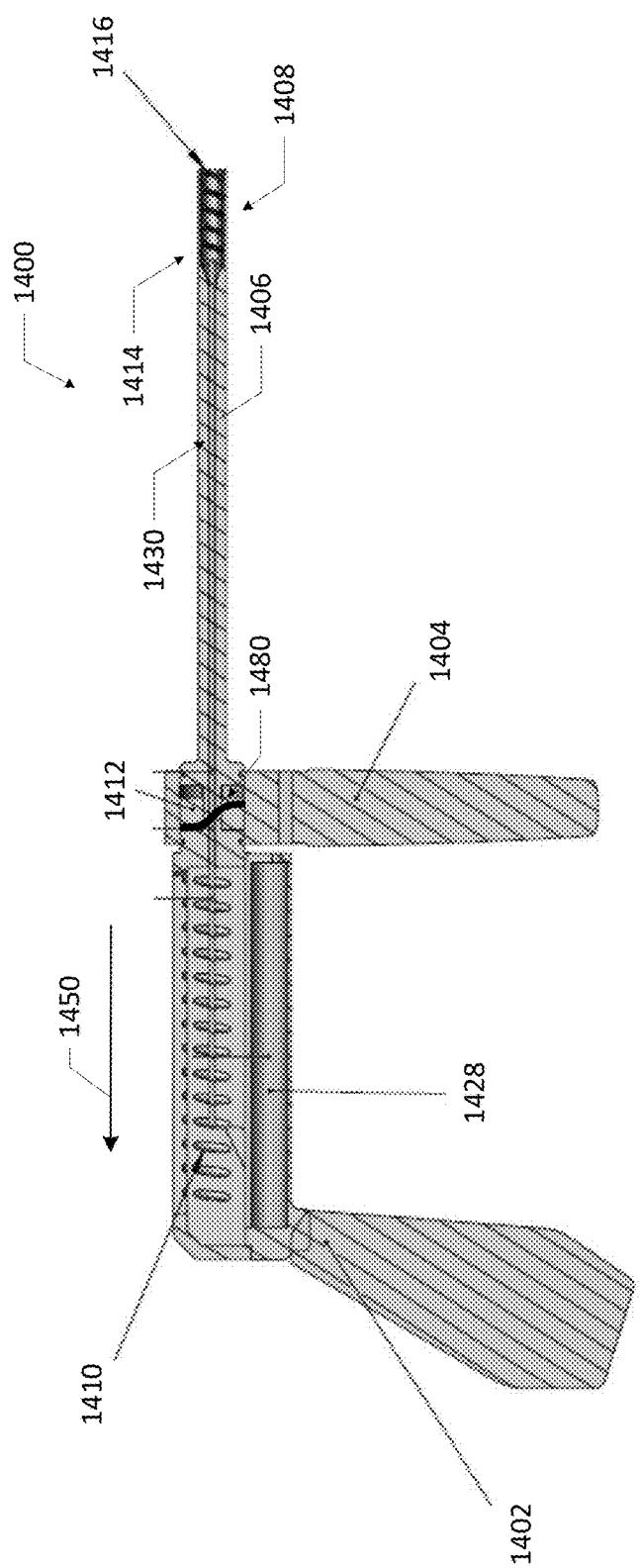
Figure 15:
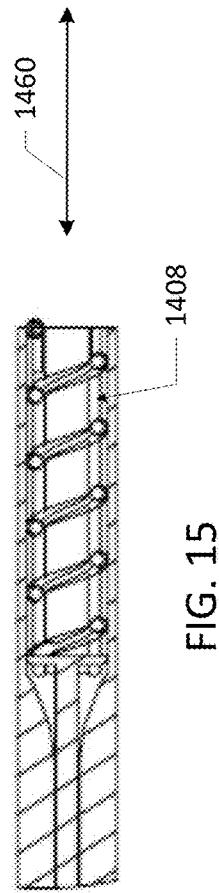

FIGS. 14-19 are various views of another insertion instrument 1400 for providing the helical suture 400 in the soft tissue 102, in accordance with various embodiments. In particular, FIG. 14 is a side cross-sectional view of the insertion instrument 1400, FIG. 15 is a detailed side cross-sectional view of a portion of a needle assembly 1430 in the needle chamber 1416 of the insertion instrument 1400, FIG. 16 is a side view of the insertion instrument 1400, FIG. 17 is a top view of the insertion instrument 1400, FIG. 18 is a front view of the insertion instrument 1400, and FIG. 19 is a rear view of the insertion instrument 1400.

The insertion instrument 1400 may include a needle assembly 1430 that may take the form of any suitable ones of the embodiments discussed above with reference to the insertion instrument 900 (FIGS. 9-13) or insertion instrument 2700. In particular, the needle assembly 1430 may include a body 1406 (which may take the form of any suitable ones of the embodiments of the body 924) and a helix-shaped needle 1408 (which may take the form of any suitable ones of the embodiments of the helix-shaped needle 902 or 2702). The needle assembly 1430 may be disposed partially within a needle chamber 1416 and partially within a slide component 1410 (e.g., as illustrated in FIGS. 14 and 15). In particular, the helix-shaped needle 1408 may have a longitudinal axis 1460 defined analogously as discussed above with reference to the longitudinal axis 920 of the helix-shaped needle 902 of the insertion instrument 900 (FIG. 9) or 2720 of the helix-shaped needle 2702 of the insertion instrument 2700 (FIG. 27).

The slide component 1410 of the insertion instrument 1400 may be configured to cause the needle assembly 1430 to rotate upon linear translation of the slide component 1410 in the direction indicated by the arrow 1450. In particular, the slide component 1410 may house a helical bearing, a portion of the body 1406 of the needle assembly 1430, and rifled sidewalls that articulate with the helical bearing as the slide component 1410 translates in the direction indicated by the arrow 1450 to cause rotation of the needle assembly 1430. The slide component 1410 may be coupled to a trigger lever 1404 such that, as the trigger lever 1404 moves toward a rear handle 1402 (e.g., in the direction indicated by the arrow 1450) and away from the soft tissue 102 (not shown, but positioned proximate to the helix-shaped needle 1408), the slide component 1410 also translates in the direction indicated by the arrow 1450, causing the needle assembly 1430 to rotate, the opposite motion causes it to rotate the other direction and could be used for a helix-shaped needle having an opposite direction of rotation. The direction of rotation of the needle assembly 1430 upon translation of the slide component 1410 is such that the helix-shaped needle 1408 is driven into the soft tissue 102 when the insertion instrument 1400 is appropriately applied to the soft tissue 102. The trigger lever 1404 may be biased away from movement toward the rear handle 1402 by a recoil spring in the recoil spring chamber 1428. The recoil spring may have any suitable spring constant, such as approximately 590 Newtons/meter (e.g., +/− 20 Newtons/meter).

The insertion instrument 1400 may include a gripping portion 1414. The gripping portion 1414 may be coupled to a grip articulator 1412, which may be in turn coupled to the trigger lever 1404 via a channel 1480. The trigger lever 1404, the grip articulator 1412, and the gripping portion 1414 may be arranged such that the trigger lever 1404 extends perpendicularly from the longitudinal axis 1460 of the helix-shaped needle 902 or 2702 and rotating the trigger lever 1404 around the longitudinal axis 1460 causes the gripping portion 1414 to close on and grip the soft tissue 102 disposed against the needle chamber 1416. In particular, rotation of the trigger lever 1404 forces concentric movement by means of the channel 1480, causing pushrods of the gripping portion 1414 to open and close teeth of the gripping portion 1414. A "tooth" with a fixed position on the inside of the trigger lever 1404 acts as a male piece to the channel 1480. Because the trigger lever 1404 and thus the tooth is fixed in relation to the longitudinal axis 1460, but the grip articulator 1412 is not (having some amount of play, e.g., approximately 10 millimeters), as the trigger lever 1404 is rotated perpendicular to the longitudinal axis 1460, the tooth exerts force upon the walls of the channel 1480. Because the tooth is not fixed along the longitudinal axis 1460, the tooth will slide forward or backward depending on the direction of rotation of the trigger lever 1404. This opens or closes gripping teeth of the gripping portion 1414 as a distal end of the grip articulator 1412 is fixed on a planar side of a gripping tooth. As discussed below with reference to FIGS. 25 and 26, a proximal end of a gripping tooth is fixed onto the needle chamber 1416 with a cross pin, acting as an axis of rotation without translation. As a push rod of the grip articular 1412 extends out, the push rod exerts force onto the midpoint of the gripping tooth, which creates rotation about the fixed axis. FIG. 18 depicts the trigger lever 1404 after a small rotation around the longitudinal axis 1460, and an embodiment of the gripping mechanism is discussed in further detail below with reference to FIGS. 25-26.

Once the soft tissue 102 has been gripped by the gripping portion 1414, translating the trigger lever 1404 along the longitudinal axis 1460 away from the soft tissue 102 (e.g., in the direction indicated by the arrow 1450) may cause the helix-shaped needle 1408 to rotate while the gripping portion 1414 is also caused to pull the soft tissue 102 in the direction indicated by the arrow 1450. The result of these substantially simultaneous operations is the rotation of the helix-shaped needle 1408 into the soft tissue 102 as the soft tissue 102 is pulled onto and along the helix-shaped needle 1408. In some embodiments, the helix-shaped needle 1408 may not translate with reference to the rear handle 1402 during use of the insertion instrument 1400 to provide a helical suture 400 to the soft tissue 102. Instead, the gripping portion 1414 may cause the soft tissue 102 to be pulled toward the rear handle 1402 while the helix-shaped needle 1408 rotates but does not translate. In other embodiments (not shown), the helix-shaped needle 1408 may translate in the direction opposite to the arrow 1450 and rotate to provide the helical suture 400 to the soft tissue 102 while the gripping portion 1414 may not translate with reference to the rear handle 1402.

The insertion instrument 1400 may be used to provide a helical suture 400 to the soft tissue 102 by having a human operator grasp the rear handle 1402 and the trigger lever 1404, position the needle chamber 1416 against the soft tissue 102, rotate the trigger lever 1404 around the longitudinal axis 1460 of the helix-shaped needle 1408 to cause the gripping portion 1414 to grip the soft tissue 102, squeeze the trigger lever 1404 towards the rear handle 1402 (against the spring force provided by the recoil spring in the recoil spring chamber 1428) to cause the gripping portion 1414 to pull the soft tissue 102 over the helix-shaped needle 1408 and simultaneously cause the helix-shaped needle 1408 to rotate into the soft tissue 102 (thereby moving suture material coupled to the helix-shaped needle 1408 through the soft tissue 102 to form the helical suture 400). When insertion is complete, an end of the suture material proximate to the distal end of the helix-shaped needle 1408 may be secured within or external to the soft tissue 102 (e.g., by grasping the end with an arthroscopic suture grabber, or as discussed below with reference to FIGS. 20 and 21) and the insertion instrument 1400 may be removed by reversing the operations discussed above. Removal of the insertion instrument 1400 from the soft tissue 102 may also pull the helical suture 400 "taut," providing an even and correct amount of tension in each turn of the helical suture 400. In some examples, the suture is pulled taught by the human operator, for example by applying a load to the suture material that extends from the soft tissue, for example a load of about 5 N to about 20 N, such that the helical suture is tightened in the tissue. A tensiometer can be used to measure the tension, such that this is not over-applied, for example a tensiometer that provides a visual or audible indication of proper tension. Such a tensiometer could be coupled to any of the devices disclosed herein.

Figure 32:
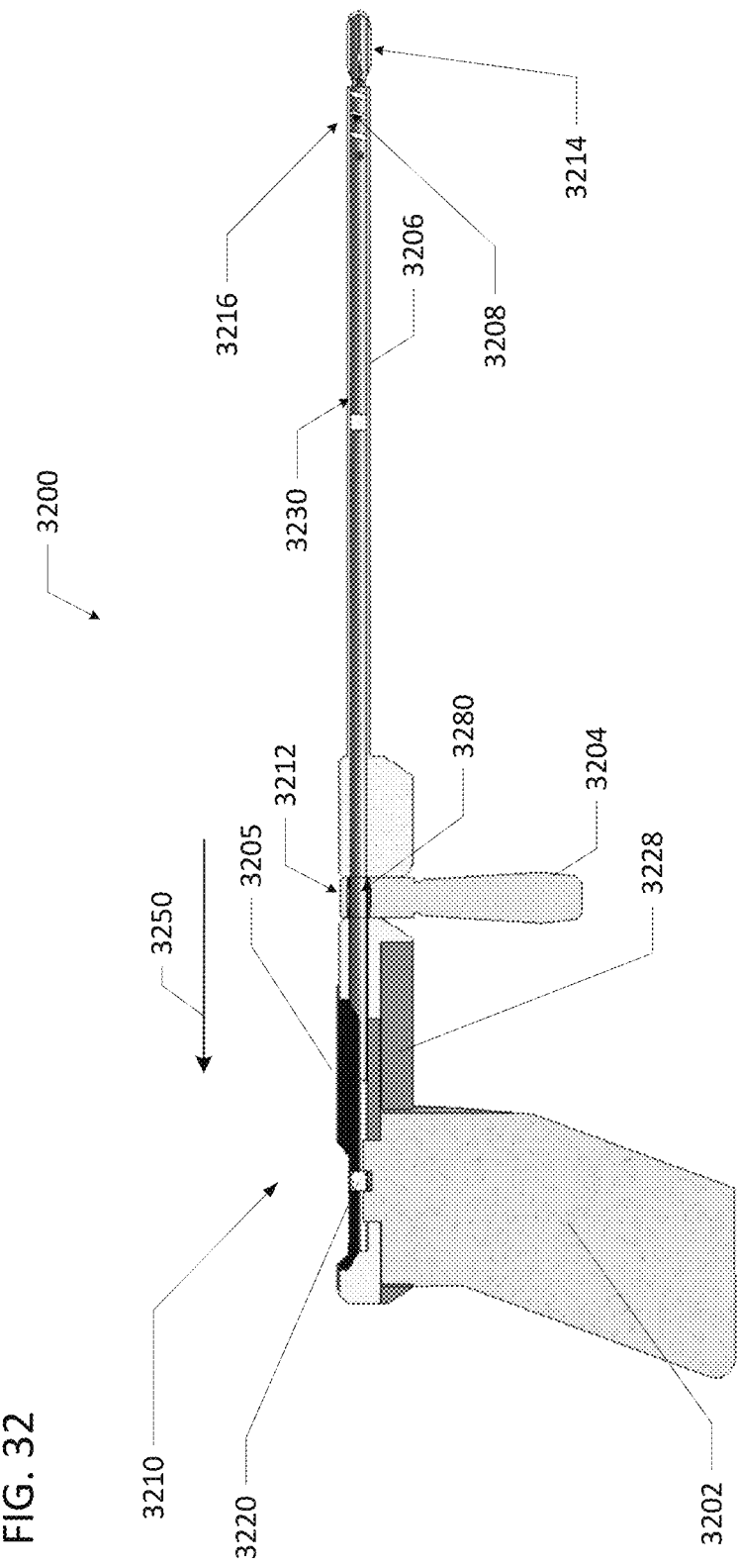
Figure 35:
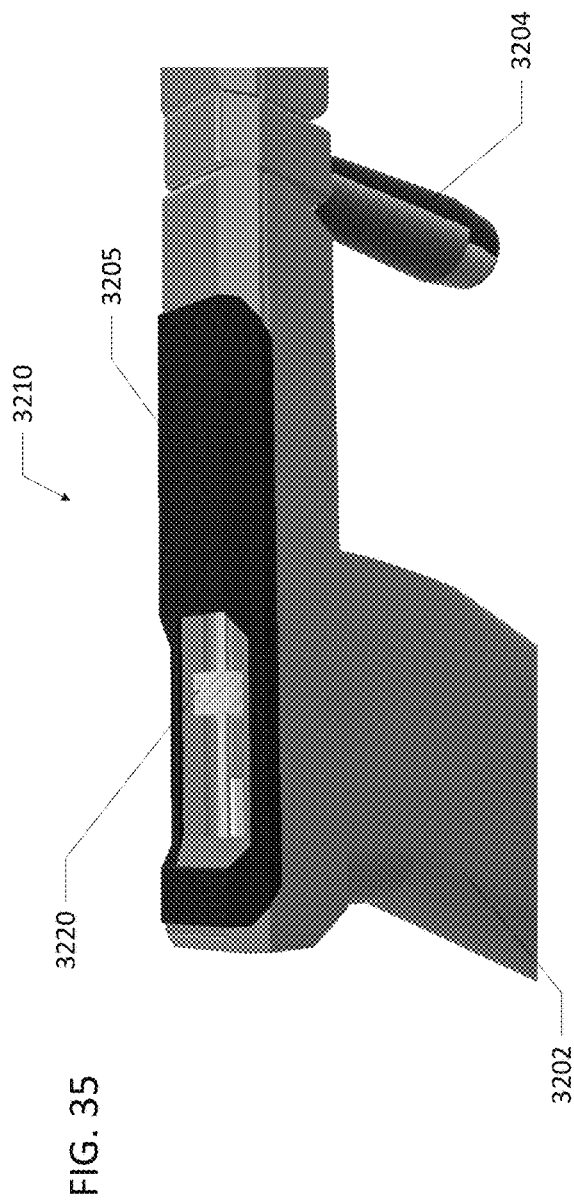
Figure 36:
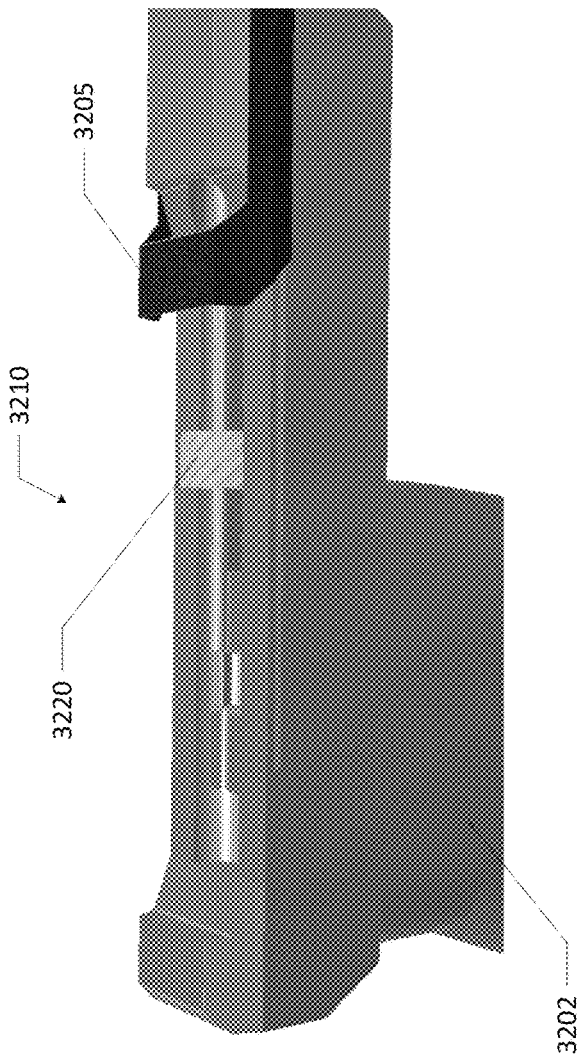

FIGS. 32-36 are various views of another insertion instrument 3200 for providing the helical suture 400 in the soft tissue 102, in accordance with various embodiments. In particular, FIGS. 32 and 33 are perspective views of the insertion instrument 3200 is a side cross-sectional view of the insertion instrument 3200. FIGS. 35 and 36 are perspective views of a portion of the slide element of the insertion instrument 3200. FIG. 36 is a side cross-sectional view of the insertion instrument 1400.

The insertion instrument 3200 may include a needle assembly 3230 that may take the form of any suitable ones of the embodiments discussed above with reference to the insertion instrument 900 (FIG. 9-13) or 2700 (FIGS. 27-31). In particular, the needle assembly 3230 may include a body 3206 (which may take the form of any suitable ones of the embodiments of the body 924 or 2724) and a helix-shaped needle 3208 (which may take the form of any suitable ones of the embodiments of the helix-shaped needle 902, or 2702). The needle assembly 3230 may be disposed partially within a needle chamber 3216 and partially within a slide component 3210 (e.g., as illustrated in FIGS. 32). In particular, the helix-shaped needle 3208 may have a longitudinal axis 3260 defined analogously as discussed above with reference to the longitudinal axis 920 of the helix-shaped needle 902 of the insertion instrument 900 (FIG. 9) or the longitudinal axis 2720 of the helix-shaped needle 2702 of the insertion instrument 2700 (FIG. 27).

The slide component 3210 of the insertion instrument 3200 may be configured to cause the needle assembly 3230 to rotate upon linear translation of the slide component 3210 in the direction indicated by the arrow 3250. In particular, the slide component 3210 may house a helical bearing, a portion of the body 3206 of the needle assembly 3230, and rifled sidewalls that articulate with the helical bearing 3220 as the slide component 3210 translates in the direction indicated by the arrow 3250 to cause rotation of the needle assembly 3230. The slide component 3210 may be coupled to a trigger lever 3204 such that, as the trigger lever 3204 moves toward a rear handle 3202 (e.g., in the direction indicated by the arrow 3250) and away from the soft tissue 102 (not shown, but positioned proximate to the helix-shaped needle 3208), the slide component 3210 also translates in the direction indicated by the arrow 3250, causing the needle assembly 3230 to rotate, the opposite motion causes it to rotate the other direction and could be used for a helix-shaped needle having an opposite direction of rotation. The direction of rotation of the needle assembly 3230 upon translation of the slide component 3210 is such that the helix-shaped needle 3208 is driven into the soft tissue 102 when the insertion instrument 3200 is appropriately applied to the soft tissue 102. The trigger lever 3204 may be biased away from movement toward the rear handle 3202 by a recoil spring in the recoil spring chamber 3228. The recoil spring may have any suitable spring constant, such as approximately 590 Newtons/meter (e.g., +/− 20 Newtons/meter).

The insertion instrument 3200 may include a gripping portion 3214. The gripping portion 3214 may be coupled to a grip articulator 3212, which may be in turn coupled to the trigger lever 3204 via a channel 3280. The trigger lever 3204, the grip articulator 3212, and the gripping portion 3214 may be arranged such that the trigger lever 3204 extends perpendicularly from the longitudinal axis 3260 of the helix-shaped needle 902 and rotating the trigger lever 3204 around the longitudinal axis 3260 causes the gripping portion 3214 to close on and grip the soft tissue 102 disposed against the needle chamber 3216. In particular, rotation of the trigger lever 3204 forces concentric movement by means of the channel 3280, causing pushrods of the gripping portion 3214 to open and close teeth of the gripping portion 3214. A "tooth" with a fixed position on the inside of the trigger lever 3204 acts as a male piece to the channel 3280. Because the trigger lever 3204 and thus the tooth is fixed in relation to the longitudinal axis 3260, but the grip articulator 3212 is not (having some amount of play, e.g., approximately 10 millimeters), as the trigger lever 3204 is rotated perpendicular to the longitudinal axis 3260, the tooth exerts force upon the walls of the channel 3280. Because the tooth is not fixed along the longitudinal axis 3260, the tooth will slide forward or backward depending on the direction of rotation of the trigger lever 3204. This opens or closes gripping teeth of the gripping portion 3214 as a distal end of the grip articulator 3212 is fixed on a planar side of a gripping tooth. As discussed below with reference to FIGS. 25 and 26, a proximal end of a gripping tooth is fixed onto the needle chamber 3216 with a cross pin, acting as an axis of rotation without translation. As a push rod of the grip articular 3212 extends out, the push rod exerts force onto the midpoint of the gripping tooth, which creates rotation about the fixed axis. FIG. 18 depicts the trigger lever 3204 after a small rotation around the longitudinal axis 3260.

Once the soft tissue 102 has been gripped by the gripping portion 3214, translating the trigger lever 3204 along the longitudinal axis 3260 away from the soft tissue 102 (e.g., in the direction indicated by the arrow 3250) may cause the helix-shaped needle 3208 to rotate while the gripping portion 3214 is also caused to pull the soft tissue 102 in the direction indicated by the arrow 3250. The result of these substantially simultaneous operations is the rotation of the helix-shaped needle 3208 into the soft tissue 102 as the soft tissue 102 is pulled onto and along the helix-shaped needle 3208. In some embodiments, the helix-shaped needle 3208 may not translate with reference to the rear handle 3202 during use of the insertion instrument 3200 to provide a helical suture 400 to the soft tissue 102. Instead, the gripping portion 3214 may cause the soft tissue 102 to be pulled toward the rear handle 3202 while the helix-shaped needle 3208 rotates but does not translate. In other embodiments (see FIGS. 33 and 34), the helix-shaped needle 3208 may translate in the direction opposite to the arrow 3250 and rotate to provide the helical suture 400 to the soft tissue 102 while the gripping portion 3214 may not translate with reference to the rear handle 3202.

The insertion instrument 3200 may be used to provide a helical suture 400 to the soft tissue 102 by having a human operator grasp the rear handle 3202 and the trigger lever 3204, position the needle chamber 3216 against the soft tissue 102, rotate the trigger lever 3204 around the longitudinal axis 3260 of the helix-shaped needle 3208 to cause the gripping portion 3214 to grip the soft tissue 102, squeeze the trigger lever 3204 towards the rear handle 3202 (against the spring force provided by the recoil spring in the recoil spring chamber 3228) to cause the gripping portion 3214 to pull the soft tissue 102 over the helix-shaped needle 3208 and simultaneously cause the helix-shaped needle 3208 to rotate into the soft tissue 102 (thereby moving suture material coupled to the helix-shaped needle 3208 through the soft tissue 102 to form the helical suture 400). Removal of the insertion instrument 3200 from the soft tissue 102 may also pull the helical suture 400 "taut," providing an even and correct amount of tension in each turn of the helical suture 400.

Use of the insertion instruments disclosed herein (e.g., the insertion instrument 900 or 2700 or the insertion instrument 1400 or 3200) may enable the provision of the helical suture 400 to the soft tissue 102 with speed and accuracy. For example, use of the insertion instrument 1400 or 2700 may enable an operator to perform one motion to cause multiple turns of the helical suture 400 to be formed.

In some embodiments, the insertion instrument 1400 or the insertion instrument 3200 may make an audible "click" or other sound as the helical suture 400 is formed to indicate when a turn has been completed. The purpose of the "audible click" is to provide tactile and aural feedback as to the position of the coil in visually diminished circumstances (e.g., when a surgeon cannot see the state of needle deployment). Each click would essentially indicate one full turn of suture loop and thus a predetermined amount of suture depth (e.g., based on the turn angle). The mechanical feature creating the audible click may include a series of notches along the longitudinal axis 1460 or the longitudinal axis 3260 within the recoil spring chamber 1428 or the recoil spring chamber 3228 over which an opposing notch on the trigger lever 1404 the trigger lever 3204 would "trip" as it is engaged along the longitudinal axis 1460 or the longitudinal axis 3260.

During use, the needle assembly 1430 or 3230 may come sterilely packaged and preloaded with suture material. The packaging may be loaded intra-operatively and loaded into the needle chamber 1416 of the insertion instrument 1400 or 3216 of the insertion instrument 3200. After the insertion instrument 1400, or 3200 has been used to form a helical suture 400, the needle assembly 1430 or 3230 may be disposed of and the remainder of the insertion instrument 1400 or 3200 may be reloaded with another needle assembly 1430 or 3230 to form another helical suture 400, or the remainder of the insertion instrument 1400 or 3200 may be cleaned (e.g., autoclaved) for another procedure. In this manner, the remainder of the insertion instrument 1400 or 3200 may be reusable and kept as a permanent instrument. In some examples, the needle assembly 1430 or 3230 can be used multiple times within the same surgical procedure. In some examples, the insertion instrument 900 and/or 2700 may be a single suture passage device. In some examples the insertion instrument 900 and/or 2700 is/are intended for multiple suture passages. One needle used per surgery, but can be used as many times as desired during that surgical procedure.

The embodiment of the helical suture 400 illustrated in FIGS. 6-8 is depicted as having two "free" ends of suture material at either end of the helical suture 400. These free ends may be knotted or otherwise secured to prevent the helical suture 400 from coming undone as the helical suture 400 undergoes force. In other embodiments of the helical suture 400, the helical suture 400 may have a toggle at one end that serves to "lock" one end of the helical suture 400 on the outside of the soft tissue 102 and prevent that end of the helical suture 400 from retreating into the soft tissue 102.

Figure 20:
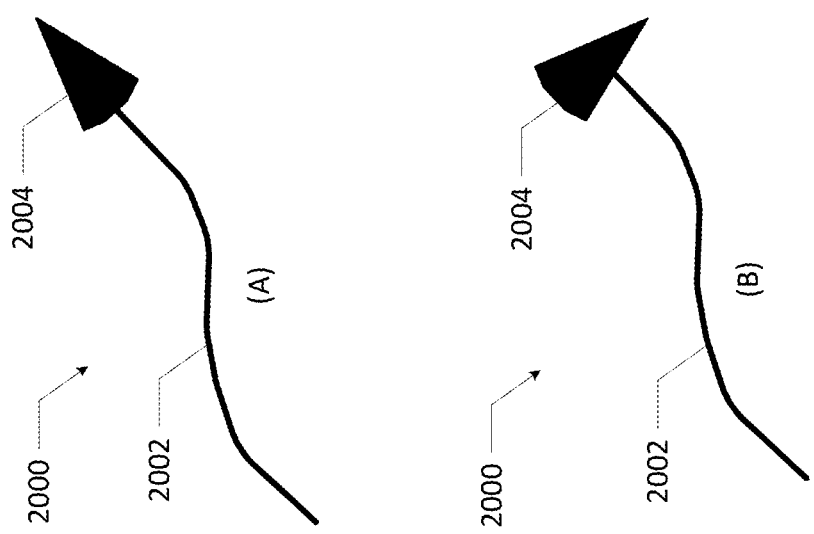
FIG. 20 illustrates a suture material having a toggle, in accordance with various embodiments.

FIG. 20 illustrates a suture material 2000 having a toggle 2004, in accordance with various embodiments. The toggle 2004 may be permanently attached to one end of the suture body 2002. The suture body 2002 may be formed of any suitable suture material, as discussed above. The toggle 2004 may also be formed from any suitable material that will not undergo deformation or failure when the helical suture 400 experiences normal physiological forces. Examples of materials that may be used in various embodiments include plastics and metals, such as a medical grade tungsten or aluminum, tantalum alloy, polyetheretherketone (PEEK), and biodegradable and non-biodegradable synthetics such as reaction polymers and bioplastics. In some embodiments, the toggle 2004 may be a tungsten arc tip permanently attached to the end of the suture body 2002.

The toggle 2004, when loaded into an insertion instrument (e.g., the insertion instrument 900 or the insertion instrument 1400) may serve as the tip of a helix-shaped needle (e.g., the helix-shaped needle 902 or the helix-shaped needle 1408). In particular, the suture body 2002 may be loaded into a recess in the helix-shaped needle (e.g., the recess 904) and the toggle 2004 may sit at the distal end of the helix-shaped needle (e.g., the end 914). In some embodiments, the toggle 2004 may be dimensioned to have a base that has approximately the same outer dimensions as the outer dimensions of the end of the helix-shaped needle (e.g., the same outer radius 918 of the end 914 of the helix-shaped needle 902).

Figure 21:
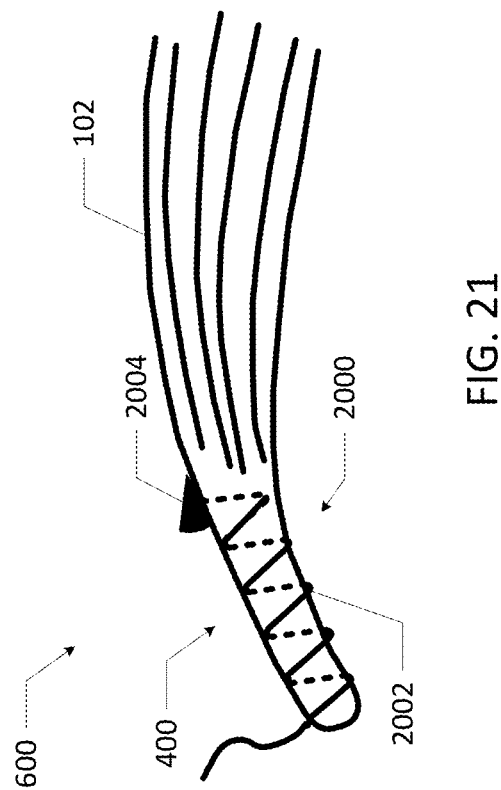
FIG. 21 is a cross-sectional view of a helical suture formed from a suture material having a toggle, in accordance with various embodiments.

The suture body 2002 may be coupled to the toggle 2004 in a manner that allows the toggle 2004 to rotate relative to the suture body 2002. Illustration (A) of FIG. 20 depicts the toggle 2004 in a "needle tip" orientation (e.g., the orientation of the suture material 2000 when the suture material 2000 is loaded into an insertion instrument) while illustration (B) of FIG. 20 depicts a toggle 2004 in a rotated "locked" orientation (e.g., the orientation of the suture material 2000 when the suture material 2000 has been used to form a helical suture 400 and the toggle 2004 is positioned at an outer surface of the soft tissue 102). FIG. 21 is a cross-sectional view of a helical suture 400 (in soft tissue 102) formed from the suture material 2000, wherein the toggle 2004 is positioned in the "locked" orientation relative to the suture body 2002 to prevent the end of the suture body 2002 coupled to the toggle 2004 from pulling back through into the soft tissue 102.

FIG. 22 is a flow diagram of an illustrative method 2200 for fixing soft tissue to an attachment surface, in accordance with various embodiments. The operations of the method 2200 may be discussed below with reference to the helical suture 400, but the method 2200 may be performed to fix soft tissue to an attachment surface using any desired helical suture.

At 2202, a helical suture may be provided in soft tissue. The soft tissue may have a longitudinal axis along which the soft tissue undergoes tension under normal physiological conditions, and a longitudinal axis of the helical suture in the soft tissue may be oriented parallel to the longitudinal axis of the soft tissue. For example, as illustrated in FIGS. 6-8, a helical suture 400 may be provided in soft tissue 102. The soft tissue 102 may have a longitudinal axis 104 along which the soft tissue 102 undergoes tension under normal physiological conditions. A longitudinal axis 410 of the helical suture 400 in the soft tissue 102 may be oriented parallel to the longitudinal axis 104 of the soft tissue 102. The soft tissue may be, for example, a tendon. In some embodiments, the helical suture may include at least two turns of suture material. In some embodiments, the helical suture may have a turn angle between 20 degrees and 60 degrees (e.g., 45 degrees).

At 2204, the helical suture may be secured to an attachment surface. The attachment surface may be, for example, a bone, other soft tissue, or any of the other example attachment surfaces discussed herein. For example, as illustrated in FIG. 6-8, the helical suture 400 may be secured to an anchor 106 in a bone 180.

Other operations may be included in the method 2200 in various embodiments. For example, the method 2200 may further include providing a second helical suture in the soft tissue, wherein a longitudinal axis of the second helical suture is oriented parallel to the longitudinal axis of the first helical suture. The method 2200 may also include securing the second helical suture to the attachment surface. Such an embodiment is illustrated in, for example, FIGS. 6-8.

The operation 2202 may be performed in any of a number of ways. In some embodiments, providing the helical suture in the soft tissue may include inserting a helix-shaped needle into the soft tissue, wherein suture material is secured to the needle, and rotating the helix-shaped needle to provide the helical suture in the soft tissue. For example, the helix-shaped needle 902 or 1408 may be deployed into the soft tissue 102 and rotated to form the helical suture 400 from suture material (e.g., the suture material 2000) secured to the helix-shaped needle. In some embodiments, a helix-shaped needle may be manually rotated in the soft tissue (e.g., as discussed above with reference to the insertion instrument 900) or may be rotated by a mechanical instrument (e.g., as discussed above with reference to the insertion instrument 1400).

The insertion instruments disclosed herein (e.g., the insertion instrument 900 and the insertion instrument 1400) may be disposable or reusable, and/or may have disposable or reusable components. For example, the needle assembly 1430 of the insertion instrument 1400 may be disposable, while the remainder of the insertion instrument 1400 may be reusable.

Figure 23:
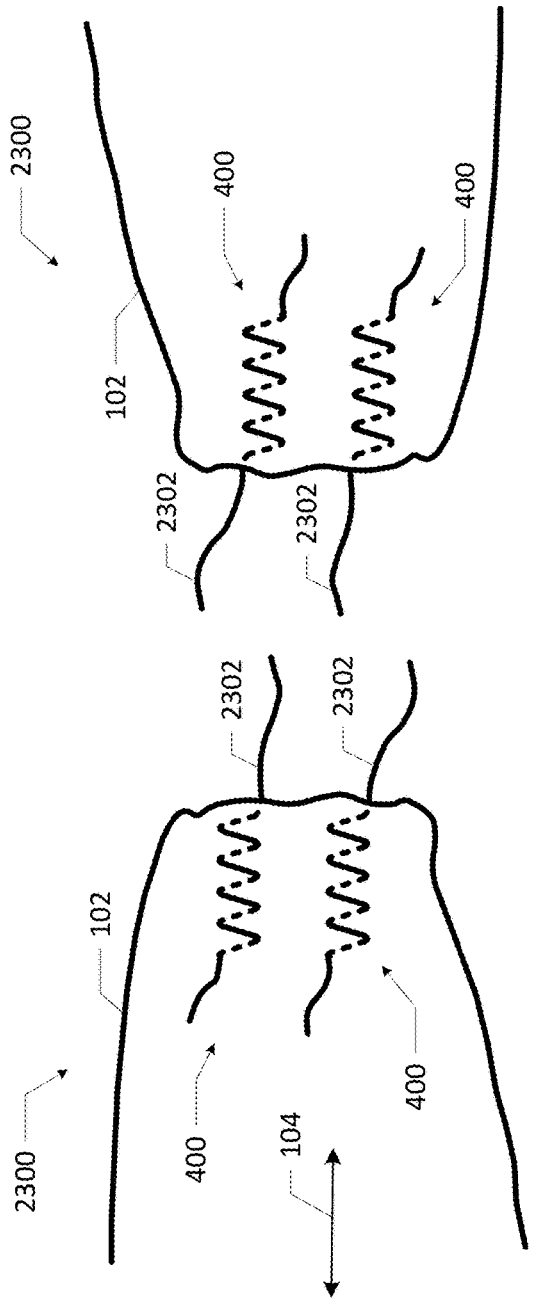
FIGS. 23-24 are views of a soft tissue-to-soft tissue repair using helical sutures, in accordance with various embodiments.
Figure 24:
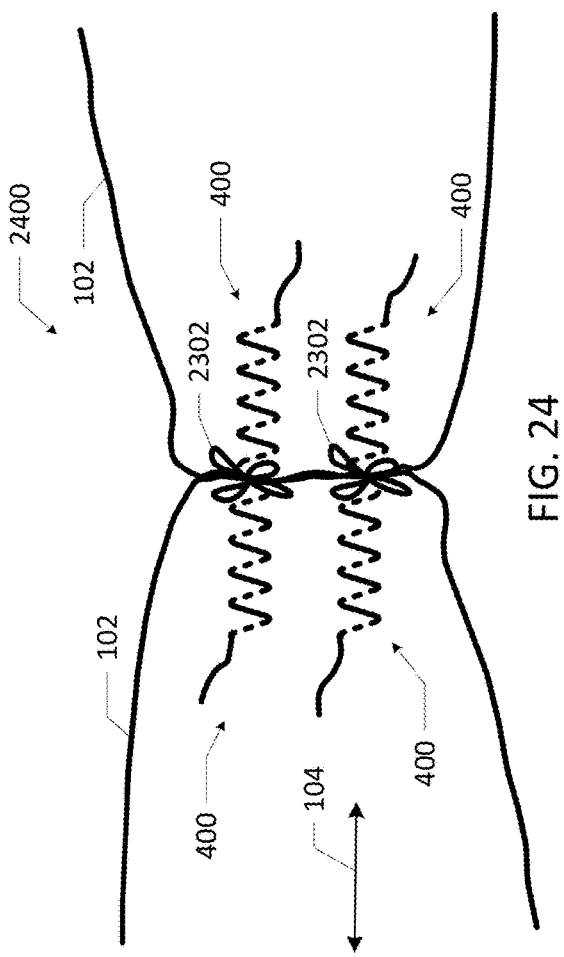

As noted above, the helical sutures 400 and related devices and techniques disclosed herein may be advantageously applied to fix soft tissue to any suitable attachment surface. For example, FIGS. 23-24 are views of a soft tissue-to-soft tissue repair using helical sutures 400, in accordance with various embodiments. In particular, FIG. 23 illustrates two portions of soft tissue 102 separated by a tear or other injury, with each portion having a helical suture arrangement 2300 disposed thereon. The helical suture arrangement 2300 may include one or more helical sutures 400 provided in the portions of soft tissue 102 (e.g., using any of the devices or techniques disclosed herein) such that the longitudinal axes of the helical sutures 400 are parallel to the longitudinal axis of the soft tissue 102 (e.g., as discussed above with reference to FIGS. 6-8). The pattern of helical sutures 400 in the helical suture arrangement 2300 may be mirrored in each of the portions of the soft tissue 102 so that each helical suture 400 has a corresponding helical suture 400 in the other portion of the soft tissue 102. Free ends 2302 of suture material may extend from the helical sutures 400.

FIG. 24 depicts a helical suture arrangement 2400 to achieve the repair of the soft tissue 102 by joining the two portions of the soft tissue 102 and tying the free ends 2302 of the corresponding helical sutures 400 of the portions of the soft tissue 102 into a knot (or otherwise securing the free ends 2302 of the corresponding helical sutures 400 to each other). The helical suture arrangement 800 is thus an example of a soft tissue-to-soft tissue repair using the helical sutures 400, and the systems and methods disclosed herein may be used in any similar or other suitable settings.

Figure 25:
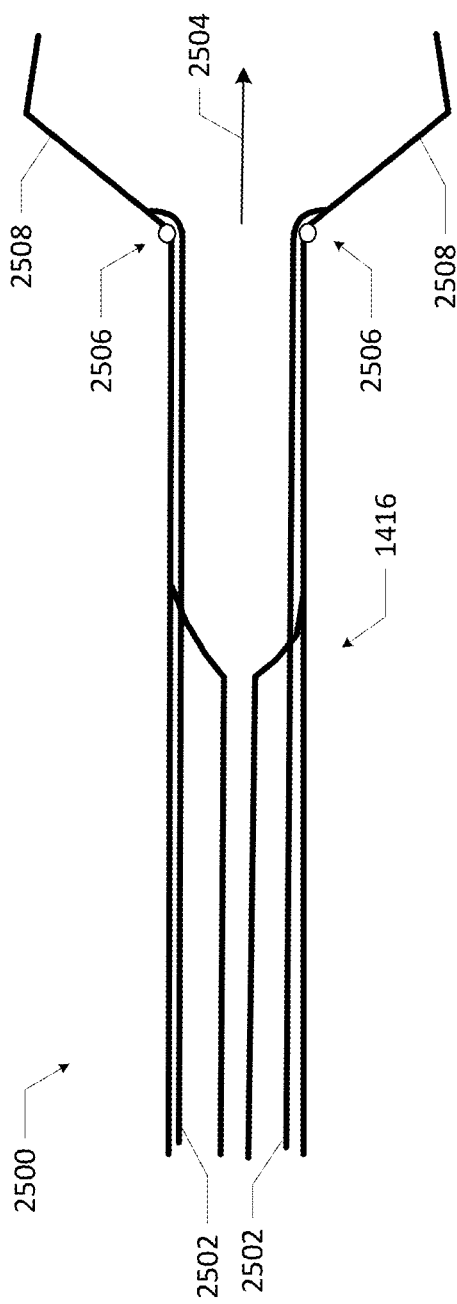
FIGS. 25-26 are cross-sectional side views of the operation of a gripping mechanism of the insertion instrument of FIGS. 14-19, in accordance with various embodiments.
Figure 26:
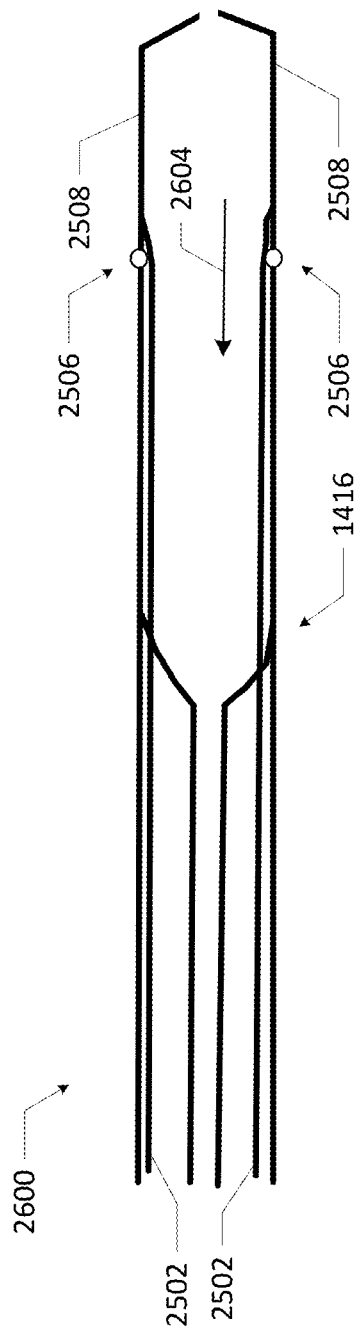

FIGS. 25-26 are cross-sectional side views of the operation of a gripping mechanism of the insertion instrument 1400 of FIGS. 14-19 and 3200 of FIGS. 32-36, in accordance with various embodiments. In particular FIG. 25 depicts gripping teeth 2508 of the gripping portion 1414 in an open configuration 2500 and FIG. 26 depicts the gripping teeth 2508 in a closed or gripping configuration 2600. The gripping portion 1414 includes push rods 2502 in the needle chamber 1416 which, when translated in the direction indicated by the arrow 2504, cause the gripping teeth 2508 to rotate about the cross-pin axes 2506 and to "open." When the push rods 2502 translate in the direction indicated by the arrow 2604, the gripping teeth 2508 rotate in the opposite direction about the cross-pin axes 2506 and the gripping teeth "close" on each other to grip any soft tissue therebetween.

As discussed above, when the soft tissue undergoes deformation due to tension forces and the helical suture 400 "lengthens" as a result, the helical suture 400 directs the tension forces both normally (into the tissue "inside" the helical suture 400 to compress that tissue) and tangentially (in the directions tangent to the helical suture 400). This distribution of forces may improve the "grip" of the helical suture 400 on the soft tissue when the soft tissue undergoes tension, reducing the likelihood of repair failure. This achieves a desirable redistribution of forces, and any braided or other suture geometry that achieves this redistribution of forces under tension may be within the scope of this disclosure.

Figure 39:
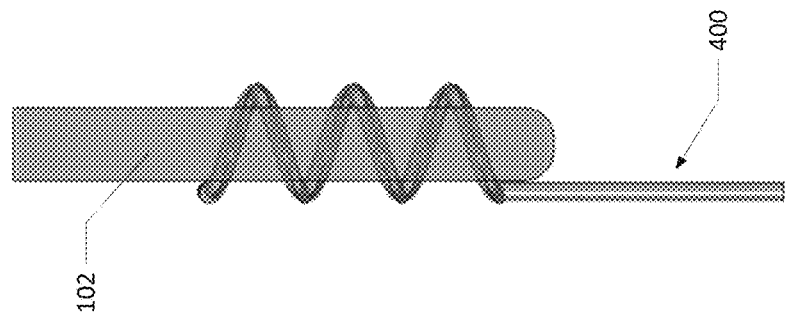
FIGS. 37A-39 are various views of double helical sutures, in accordance with various embodiments as would sit within soft tissue.
Figure 38A:
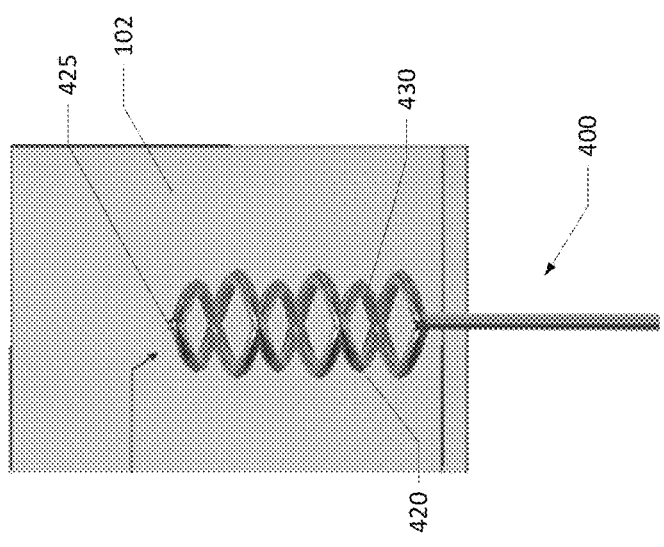
Figure 38B:
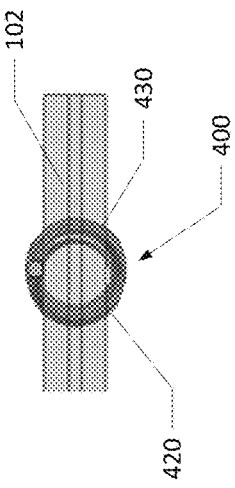
Figure 37A:
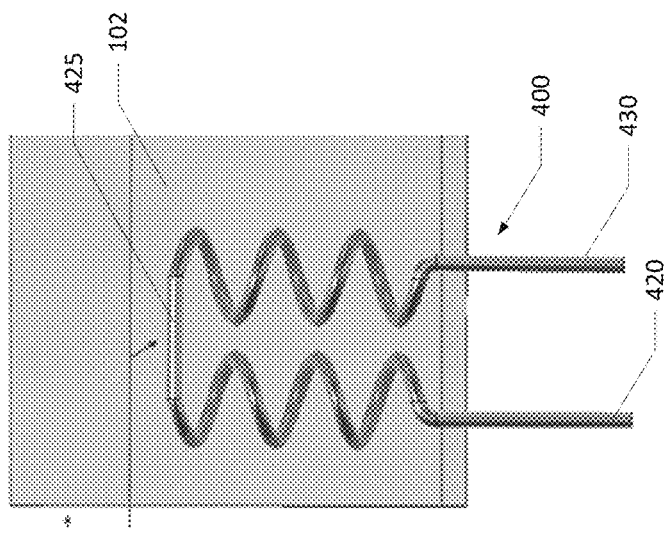
Figure 37B:
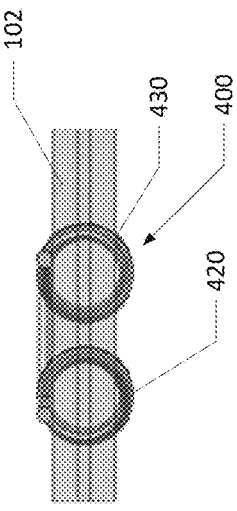

FIGS. 37A-39 are various views of helical sutures 400 disposed in the soft tissue 102 using two helix-shaped needles, such as 902 or 2702 where the direction of rotation of the helices of the two helix-shaped needles is opposite. FIGS. 37A and 37B show two parallel sutures 420 and 430, bridged by suture material 425. FIGS. 37A and 37B show two parallel and overlapping sutures 420 and 430, bridged by suture material 425. FIG. 39 shows suture 400 passing over and under soft tissue 102. The two suture strands 420 and 430 are composed on a single suture filament. One helix-shaped needle have a direction of rotation is used to anchor the first strand, strand 420 in the soft tissue 102, a second helix-shaped needle is then used to pick up the remaining suture material and guide it back through the soft tissue, strand 430. This configuration leaves no loose ends of suture except at the lateral edge of tendon requiring repair of the soft tissue.

The invention claimed is:

1. A method for fixing soft tissue of a subject to an attachment surface, comprising:
    passing a first end of a suture through the soft tissue of the subject a plurality of times to form a first helix having a first longitudinal axis within the soft tissue,
    passing a second end of the suture through the soft tissue of the subject a plurality of times to form a second helix that is distinct from the first helix, the second helix having a second longitudinal axis within the soft tissue, wherein the first axis and second axis are different axes formed by the suture within the soft tissue,
    wherein the soft tissue has a longitudinal axis and wherein at least one of the first longitudinal axis and the second longitudinal axis of the suture in the soft tissue is oriented parallel to the longitudinal axis of the soft tissue, wherein the soft tissue undergoes tension, under normal physiological conditions, along the longitudinal axis of the soft tissue; and
    securing the first end of the suture to the attachment surface, wherein the attachment surface is a different tissue or material than the soft tissue being fixed.

2. The method of claim 1, wherein the soft tissue comprises a tendon.

3. The method of claim 1, wherein the suture comprises at least two turns of suture material.

4. The method of claim 1, further comprising inserting a bone anchor into a bone, and wherein securing the first end of the suture to the attachment surface comprises securing the first end of the suture to the bone anchor.

5. The method of claim 1, wherein the attachment surface comprises a bone, tendon, soft tissue, allograft material, xenograft material, or a synthetic material.

6. The method of claim 1, wherein the first helix comprises a turn angle between approximately 20 degrees and approximately 70 degrees.

7. The method of claim 1, further comprising securing the second end of the suture to the attachment surface.

8. The method of claim 1, wherein the second longitudinal axis of the second end of the suture is oriented substantially parallel to the first longitudinal axis of the first end of the suture.

9. The method of claim 1, wherein the second longitudinal axis of the second end of the suture is oriented non-parallel to the first longitudinal axis of the first end of the suture.

10. The method of claim 1, wherein the first helix and the second helix have opposite directions of rotations.

11. The method of claim 1, wherein the first helix and the second helix have the same direction of rotation.

12. The method of claim 1, wherein the first helix is intertwined with the second helix.

13. The method of claim 1, wherein passing a first end of a suture comprises:
passing a helix-shaped needle through the soft tissue, wherein the first end of the suture is coupled to the helix-shaped needle; and
rotating the helix-shaped needle to pass the first end of the suture through the soft tissue.

14. The method of claim 13, wherein rotating the helix-shaped needle advances the helix-shaped needle through the soft tissue.

15. The method of claim 13, wherein rotating the helix-shaped needle comprises:
linearly translating a slide component of an insertion instrument comprising the helix-shaped needle, wherein the linear translation of the slide component causes rotation of the helix-shaped needle.

16. The method of claim 15, wherein linearly translating the slide component comprises linearly translating a trigger lever toward a rear handle along the longitudinal axis of the helix-shaped needle to cause translation of the slide component, which causes rotation of the helix-shaped needle.

17. The method of claim 1, further comprising:
gripping, with a gripping portion of an insertion instrument comprising a helix-shaped needle, the soft tissue; and
pulling, with the gripping portion, the soft tissue toward and over the helix-shaped needle while the helix-shaped needle rotates.

18. The method of claim 17, wherein the insertion instrument comprises a trigger lever extending perpendicularly from a longitudinal axis of the helix-shaped needle, rotating the trigger lever around the longitudinal axis of the helix-shaped needle causes the gripping portion to grip the soft tissue, and translating the trigger lever along the longitudinal axis of the helix-shaped needle and longitudinal axis of the helix-shaped needle causes the helix-shaped needle to rotate.

19. The method of claim 1, wherein the suture distributes stress across the soft tissue.

20. The method of claim 1, wherein, when the soft tissue undergoes deformation due to tension forces, the suture directs the tension forces normally and tangentially with respect to the soft tissue.

21. The method of claim 1, wherein passing a first end of a suture through the soft tissue forms a first helix having a right-handed helical direction, and passing a second end of the suture through the soft tissue forms a second helix having a left-handed helical direction.

22. A method for fixing soft tissue of a subject to an attachment surface:
passing a helix-shaped needle having a tip through the soft tissue;
rotating the helix-shaped needle to provide a first helical channel in the soft tissue;
after provision of the first helical channel, securing a first end of a suture material to the tip of the helix-shaped needle;
reversing a direction of rotation of the helix-shaped needle thereby passing the suture through the soft tissue to form a first helix having a first longitudinal axis within the soft tissue;
detaching the first end from the helix-shaped needle;
repeating the passing and rotation to create a second helical channel in the soft tissue distinct from the first helical channel;
after provision of the second helical channel, securing a second end of the suture material to the tip of the helix-shaped needle;
reversing the direction of rotation of the helix-shaped needle to form a second helix having a second longitudinal axis within the soft tissue, wherein the first axis and second axis are different axes formed by the suture within the soft tissue; and
securing one or both of the first end or second end of the suture material to an attachment surface, wherein the attachment surface is a different tissue or material than the soft tissue being fixed,
passing a first end of a suture through the soft tissue of the subject a plurality of times to form a first helix having a first longitudinal axis within the soft tissue.

\* \* \* \* \*